US007157252B2

(12) United States Patent
Koibuchi et al.

(10) Patent No.: US 7,157,252 B2
(45) Date of Patent: Jan. 2, 2007

(54) GLUTAMINASE, ITS GENE AND A METHOD OF PRODUCING IT

(75) Inventors: Kyoko Koibuchi, Kawsaki (JP); Hiroaki Nagasaki, Kawsaki (JP); Ari Yuasa, Kawsaki (JP); Jiro Kataoka, Kawsaki (JP); Katsuhiko Kitamoto, Ushiku (JP)

(73) Assignee: Ajinomoto Co., Inc., Tokyo (JP)

( * ) Notice: Subject to any disclaimer, the term of this patent is extended or adjusted under 35 U.S.C. 154(b) by 365 days.

(21) Appl. No.: 10/851,337

(22) Filed: May 24, 2004

(65) Prior Publication Data

US 2004/0229322 A1 Nov. 18, 2004

Related U.S. Application Data

(62) Division of application No. 10/262,083, filed on Oct. 2, 2002, now Pat. No. 6,830,905, which is a division of application No. 09/674,507, filed as application No. PCT/JP99/02455 on May 12, 1999, now abandoned.

(30) Foreign Application Priority Data

| May 15, 1998 | (JP) | ................................ 10-134080 |
| Sep. 11, 1998 | (JP) | ................................ 10-258974 |
| Oct. 14, 1998 | (JP) | ................................ 10-292443 |
| Mar. 30, 1999 | (JP) | ................................ 11-89157 |

(51) Int. Cl.
*C12P 13/14* (2006.01)
*C12N 9/80* (2006.01)

(52) U.S. Cl. ........................................ 435/110; 435/228
(58) Field of Classification Search .................... None
See application file for complete search history.

(56) References Cited

OTHER PUBLICATIONS

Shaffer et al. An asperaginase of Aspergillus nidulans is subject to oxygen repression in addition to nitrogen metabolie repression. Mol. Gen. Genet 1988, 212, 337-341.*
T. Yano, et al., "Purification and Properties of Glutaminase From *Aspergillus Oryzae*", J. Ferment. Technol., (1988), 66, No. 2, pp. 137-143.
T. Yano, et al., Agricultural and Biological Chemistry, vol. 55, No. 2, XP-001057982, pp. 387-391, "Production and Localization of Enzymes on Soft Gel Cultivation", 1991.
K. Koibuchi, et al., Applied Microbiology and Biotechnology, vol. 54, No. 1, XP-002191327, pp. 59-68, "Molecular Cloning and Characterization of a Gene Encoding Glutaminase From *Aspergillus Oryzae*", Jul. 2000.
Takahiro Ohba, et al., Purification of *Aspergillus oryzae* sp. glutaminase and cloning its gene (part 1), Institute of Biology and Food, Feb. 2, 2004, 1 page, (with partial English translation).

* cited by examiner

*Primary Examiner*—Nashaat T. Nashed
(74) *Attorney, Agent, or Firm*—Oblon, Spivak, McClelland, Maier & Neustadt, P.C.

(57) ABSTRACT

Glutaminase is purified from an *Aspergillus oryzae*, its partial amino acid sequence is determined, a partial sequence of glutaminase gene is obtained by PCR based on the obtained information, and DNA fragments containing glutaminase gene from *Aspergillus oryzae* genomic library and cDNA library, and *Aspergillus nidulans* genomic library by hybridization using the partial sequence as a probe.

6 Claims, No Drawings

SEQUENCE LISTING

<160> NUMBER OF SEQ ID NOS: 26

<210> SEQ ID NO 1
<211> LENGTH: 4013
<212> TYPE: DNA
<213> ORGANISM: Aspergillus oryzae
<220> FEATURE:
<221> NAME/KEY: CDS
<222> LOCATION: (1174)..(1370)
<223> OTHER INFORMATION:
<220> FEATURE:

```
<221> NAME/KEY: CDS
<222> LOCATION: (1446)..(1741)
<223> OTHER INFORMATION:
<220> FEATURE:
<221> NAME/KEY: CDS
<222> LOCATION: (1800)..(2242)
<223> OTHER INFORMATION:
<220> FEATURE:
<221> NAME/KEY: CDS
<222> LOCATION: (2297)..(2880)
<223> OTHER INFORMATION:
<220> FEATURE:
<221> NAME/KEY: CDS
<222> LOCATION: (2932)..(3134)
<223> OTHER INFORMATION:
<220> FEATURE:
<221> NAME/KEY: CDS
<222> LOCATION: (3181)..(3324)
<223> OTHER INFORMATION:
<220> FEATURE:
<221> NAME/KEY: CDS
<222> LOCATION: (3380)..(3515)
<223> OTHER INFORMATION:
<220> FEATURE:
<221> NAME/KEY: CDS
<222> LOCATION: (3562)..(3628)
<223> OTHER INFORMATION:
<220> FEATURE:
<221> NAME/KEY: Intron
<222> LOCATION: (1371)..(1445)
<223> OTHER INFORMATION:
<220> FEATURE:
<221> NAME/KEY: Intron
<222> LOCATION: (1742)..(1799)
<223> OTHER INFORMATION:
<220> FEATURE:
<221> NAME/KEY: Intron
<222> LOCATION: (2243)..(2296)
<223> OTHER INFORMATION:
<220> FEATURE:
<221> NAME/KEY: Intron
<222> LOCATION: (2881)..(2931)
<223> OTHER INFORMATION:
<220> FEATURE:
<221> NAME/KEY: Intron
<222> LOCATION: (3135)..(3180)
<223> OTHER INFORMATION:
<220> FEATURE:
<221> NAME/KEY: Intron
<222> LOCATION: (3325)..(3379)
<223> OTHER INFORMATION:
<220> FEATURE:
<221> NAME/KEY: Intron
<222> LOCATION: (3516)..(3561)
<223> OTHER INFORMATION:
<220> FEATURE:
<221> NAME/KEY: sig_peptide
<222> LOCATION: (1174)..(1233)
<223> OTHER INFORMATION:
<220> FEATURE:
<221> NAME/KEY: mat_peptide
<222> LOCATION: (1234)..()
<223> OTHER INFORMATION:

<400> SEQUENCE: 1
ctcgagagac tccttgccac ctgatactat cacaattgtc ggtcacacgc gactggctac      60
tactacttcg taggcaccgt agtataccccc agtctctttta ggatggcaat accttgttgt    120
atagatgttg tagtcatgta ggattccctg agattccct gatcggacgg caagagtgac       180
cccacttcca agtattgact ccatctcagc tcgatgtatc actttcctgt ttagggcacg      240
ggagcatcac tgacggctct ctgcctcagg ccatgattgt ttcttttgtc aattcgactt     300
ctccaaatcg agctgcagat ctgtcgaccc catcccagtt gatgcagtag ctcggctacc     360
ggaagagatt tattcttagt cccttgttgg gattgggatt caccctcgct tctgtttctc    420
```

```
accgtattta tatcgcgcaa tgagattgat ccggatataa aatgtctgtg atgcactctt      480
tctcacgcac cgaggtaatc aatatcatat gctttcccct catatcactg ccgaaaagac      540
taactcggtc tacccatag tcaccagcca ctagcgcttc ttgggcctct ccttgtttgc       600
tcagtggatc taaagccaag actatcatgg ttagtgtcgg gttgtcttca ttagatcgtc      660
tgcagcccca gagtgtatcg gcttaggact ggtcgagccc gacgcggcta aggataaggt      720
acatactccc actctatcga cccttgcttg ttaatctccg atcttgtctc ctgtccaatt      780
gtcgggcttc tcctggaatt ccaggtttct ttcacctgtc gggcagccgg atcgaggccg      840
catgaattgc tcccccacag agactgacag gtcaggcgat attgggggag tcacaatcat      900
gcgcgccccc attccgcatt ccgtttctcg accctcatgc agcgtgctaa acttccatag      960
tccctcctga attgtctgcc ctgccctccg gtatgcgggc tggaccaact atataagtgt     1020
gcctaacatt ccttcagcat tcttcaggcc cacattctcg ggggcacgtt ttttggcgga     1080
tctcgatcct actctttcat tctttgaaga aacctggaat tattacgtgt ataaatgaag     1140
gatgtaccct gtgtgaatcc ctcaatacgg atc atg atg cat ttc ctc tcg ttc      1194
                                    Met Met His Phe Leu Ser Phe
                                    -20             -15 tgt ctg tcg gtg gcc tcc ctg gtg tct tac gcg gga gct gcg tca aca        1242
Cys Leu Ser Val Ala Ser Leu Val Ser Tyr Ala Gly Ala Ala Ser Thr
        -10             -5              -1  1 ttc tcc cct gcg agg cca ccc gcc ctg ccc ttg gct gtc aaa tcg ccg        1290
Phe Ser Pro Ala Arg Pro Pro Ala Leu Pro Leu Ala Val Lys Ser Pro
    5               10              15 tac ttg agc aca tgg ctc tct gcg ggc aca gat ggc ggt aat gga ggg        1338
Tyr Leu Ser Thr Trp Leu Ser Ala Gly Thr Asp Gly Gly Asn Gly Gly
20              25              30              35 tac ctg gcc ggc caa tgg cct acc ttc tgg tt  gtgagtagtc ccgagctgta     1390
Tyr Leu Ala Gly Gln Trp Pro Thr Phe Trp Phe
                40              45 gaaatgaaga catccatctt gatgtacatt ggctaaacca cgtccctcgt ggcag c        1446 ggc cag gtg acc ggc tgg gcg ggt cag atc cgg gtc gat aat tcg acc        1494
Gly Gln Val Thr Gly Trp Ala Gly Gln Ile Arg Val Asp Asn Ser Thr
            50              55              60 tac aca tgg atg ggg gcg atc cct aac acc cct acg gtg aac cag aca        1542
Tyr Thr Trp Met Gly Ala Ile Pro Asn Thr Pro Thr Val Asn Gln Thr
        65              70              75 tcc ttc gag tac acc tcg acg tcg agc gtg ttc acg atg cgt gtt ggg        1590
Ser Phe Glu Tyr Thr Ser Thr Ser Ser Val Phe Thr Met Arg Val Gly
    80              85              90 gat atg gtg gaa atg aaa gtg aaa ttc ctg tcc cct atc aca cca gat        1638
Asp Met Val Glu Met Lys Val Lys Phe Leu Ser Pro Ile Thr Pro Asp
95              100             105             110 gat ctc cgg aga cag tcg ctt gtg ttt tcc tat ctg gac gta gat gtc        1686
Asp Leu Arg Arg Gln Ser Leu Val Phe Ser Tyr Leu Asp Val Asp Val
            115             120             125 gaa tcg atc gac ggc aaa gcg cat gac ata cag gtg tac gca gac att        1734
Glu Ser Ile Asp Gly Lys Ala His Asp Ile Gln Val Tyr Ala Asp Ile
        130             135             140 tca gca g  gtaagcaaga cgacaaccca cctggaacag tgcaaatatc catctaaccg      1791
Ser Ala ggtcttag aa  tgg gcg tcc ggg gac cga aac gcc att gcg cag tgg gac       1840
            Glu Trp Ala Ser Gly Asp Arg Asn Ala Ile Ala Gln Trp Asp
                145             150             155 tat ggt gtc aca gat gat ggc gtt gcc tat cac aag gtt tac cgc caa        1888
```

```
                                                            -continued
Tyr Gly Val Thr Asp Asp Gly Val Ala Tyr His Lys Val Tyr Arg Gln
    160             165                 170 acg cag ctg ctg ttt tcc gaa aac act gag cag gcc gaa tgg ggc gag      1936
Thr Gln Leu Leu Phe Ser Glu Asn Thr Glu Gln Ala Glu Trp Gly Glu
175             180                 185                 190 tgg tac tgg gcc aca gac gac caa gat ggt ctg agc tac cag tcc gga      1984
Trp Tyr Trp Ala Thr Asp Asp Gln Asp Gly Leu Ser Tyr Gln Ser Gly
                195                 200                 205 ccg gat gtt gat gtg cga ggg gca ttc gca aag aac gga aag ttg gcg      2032
Pro Asp Val Asp Val Arg Gly Ala Phe Ala Lys Asn Gly Lys Leu Ala
            210                 215                 220 aat tcg gat gat aaa aat tat cgt gca atc tcg acc aat tgg ccc gtg      2080
Asn Ser Asp Asp Lys Asn Tyr Arg Ala Ile Ser Thr Asn Trp Pro Val
        225                 230                 235 ttt gcc ttc tcc cgc gat ctt ggc tcg gtg aag acg tct gct ggc acg      2128
Phe Ala Phe Ser Arg Asp Leu Gly Ser Val Lys Thr Ser Ala Gly Thr
    240                 245                 250 tta ttc tcc att ggc ctt gcg cag gac agt gcc ata cag tac agt ggg      2176
Leu Phe Ser Ile Gly Leu Ala Gln Asp Ser Ala Ile Gln Tyr Ser Gly
255                 260                 265                 270 aaa cct gaa ggg aca act gtg atg cct tca ctc tgg aag agc tac ttc      2224
Lys Pro Glu Gly Thr Thr Val Met Pro Ser Leu Trp Lys Ser Tyr Phe
                275                 280                 285 agc act gcg act gct gcg gtaagtggcc cactgctgtt tcggacctag             2272
Ser Thr Ala Thr Ala Ala
            290 aacataatct gaccatctat gtag ctt gag ttc ttc cat cat gat tat gct      2323
                          Leu Glu Phe Phe His His Asp Tyr Ala
                                  295                 300 gct gca gct gca cta tcg aag gat ctc gat gac cgg ata tcc aag gat      2371
Ala Ala Ala Ala Leu Ser Lys Asp Leu Asp Asp Arg Ile Ser Lys Asp
                305                 310                 315 tcc att gat gcc gct ggc cag gac tac ctg aca atc acc tcc ctc acg      2419
Ser Ile Asp Ala Ala Gly Gln Asp Tyr Leu Thr Ile Thr Ser Leu Thr
            320                 325                 330 gtc cgt caa gtc ttt gct gcc gtg caa ttg acc ggc acg ccc gag gac      2467
Val Arg Gln Val Phe Ala Ala Val Gln Leu Thr Gly Thr Pro Glu Asp
        335                 340                 345 ccc tac atc ttc atg aag gag atc tcg tcc aat ggc aac atg aac act      2515
Pro Tyr Ile Phe Met Lys Glu Ile Ser Ser Asn Gly Asn Met Asn Thr
350                 355                 360                 365 gtg gac gtc atc ttc ccc gct cac ccg atc ttt ttg tac acc aat ccc      2563
Val Asp Val Ile Phe Pro Ala His Pro Ile Phe Leu Tyr Thr Asn Pro
                370                 375                 380 gag ctc ctc aaa ctg att ctg aag cca atc tat gag att caa gag aac      2611
Glu Leu Leu Lys Leu Ile Leu Lys Pro Ile Tyr Glu Ile Gln Glu Asn
            385                 390                 395 gga aag tat ccc aac aca tac gcc atg cac gat att gga acc cac tac      2659
Gly Lys Tyr Pro Asn Thr Tyr Ala Met His Asp Ile Gly Thr His Tyr
        400                 405                 410 ccg aac gcc acg ggc cat cct aag ggc gac gac gag aaa atg cca ctc      2707
Pro Asn Ala Thr Gly His Pro Lys Gly Asp Asp Glu Lys Met Pro Leu
    415                 420                 425 gag gag tgt gga aac atg gtt atc atg gcc ctt gcc tac gcc cag aag      2755
Glu Glu Cys Gly Asn Met Val Ile Met Ala Leu Ala Tyr Ala Gln Lys
430                 435                 440                 445 gcc aag gac aac gac tat ctt tca cag cac tat ccc atc ctc aac aaa      2803
Ala Lys Asp Asn Asp Tyr Leu Ser Gln His Tyr Pro Ile Leu Asn Lys
                450                 455                 460
```

```
tgg aca aca tac ctc gtc gag gat tct att tac ccg gcg aac cag atc              2851
Trp Thr Thr Tyr Leu Val Glu Asp Ser Ile Tyr Pro Ala Asn Gln Ile
        465                 470                 475 tct acg gat gac ttt gct ggc tcg cta gc  gtaagtgata tacatacacg                2900
Ser Thr Asp Asp Phe Ala Gly Ser Leu Ala
        480                 485 acacaggcgg tgatactaat agtatgtaca g a aac cag acc aac ctg gca ttg             2953
                                  Asn Gln Thr Asn Leu Ala Leu
                                              490 aag gga atc att gga atc cag gca atg gct gtg atc agc aat acg aca              3001
Lys Gly Ile Ile Gly Ile Gln Ala Met Ala Val Ile Ser Asn Thr Thr
495                 500                 505                 510 gga cac ccg gac gat gcc tcc aac cac tcc agc att gcc aag gac tac              3049
Gly His Pro Asp Asp Ala Ser Asn His Ser Ser Ile Ala Lys Asp Tyr
                515                 520                 525 atc gcg agg tgg cag aca cta ggc gta gct cac gat gcc aat cct ccg              3097
Ile Ala Arg Trp Gln Thr Leu Gly Val Ala His Asp Ala Asn Pro Pro
        530                 535                 540 cat aca acg ctg tcg tac gga gcg aac gag act cat g gtcagttagc                 3144
His Thr Thr Leu Ser Tyr Gly Ala Asn Glu Thr His
        545                 550 cgctccgggt gcacttataa tactgacttt ctccag gg  ctt ctg tac aat ctg              3197
                                           Gly Leu Leu Tyr Asn Leu
                                                   555             560 tat gcg gat cgt gaa ttg ggc ttg aac ttg gtt cct cag tcg gtc tat              3245
Tyr Ala Asp Arg Glu Leu Gly Leu Asn Leu Val Pro Gln Ser Val Tyr
                565                 570                 575 gac atg caa aac acc ttc tat ccg acg gtg aag gag aag tat gga gtg              3293
Asp Met Gln Asn Thr Phe Tyr Pro Thr Val Lys Glu Lys Tyr Gly Val
        580                 585                 590 ccg ctc gat act cga cac gtg tac act aag g gtaagctcga tatgttcttt             3344
Pro Leu Asp Thr Arg His Val Tyr Thr Lys
                595                 600 ctaatgtttg acattgaata ttgacttgtc cccag cg  gat tgg gag ctt ttc               3396
                                          Ala Asp Trp Glu Leu Phe
                                                          605 aca gct gcg gtt gcg tcg gag agt gtc cga gac atg ttc cac cag gcg              3444
Thr Ala Ala Val Ala Ser Glu Ser Val Arg Asp Met Phe His Gln Ala
        610                 615                 620 ctc gcg acg tgg atc aac gag aca ccg acc aac cgt gcc ttt acg gat              3492
Leu Ala Thr Trp Ile Asn Glu Thr Pro Thr Asn Arg Ala Phe Thr Asp
625                 630                 635                 640 ctc tat gat acc caa act gga aa  gtaagtgttt gccaaggggc tgcttgggcc             3545
Leu Tyr Asp Thr Gln Thr Gly Asn
                645 ttgctgacca atatag t tat ccg gcg ggc att acg ttc att gcg cgg ccc              3595
                  Tyr Pro Ala Gly Ile Thr Phe Ile Ala Arg Pro
                                  650                 655 gtc atg ggt ggt gcc ttt gcg ttg tta att ctc tagagtcgtt tcattgtata            3648
Val Met Gly Gly Ala Phe Ala Leu Leu Ile Leu
660                 665                 670 ttgattttat tcgcttctgg gcgcgagtgg agacacttgc ttactttgtt tccaatttta            3708
ttattaccgt ggctatggga ccagattgac cgttgttaat agcgtacctc atacatagca            3768
tttttattct gcaaatagtg ttgttgtatt tgggtctcca ataataatgc gttcgtagac            3828
gatgctccaa aggaactatc tggtctgcaa gctgcttata tcaagcatat ataaagatct            3888
acgtatccag tcgtgcttat ccaagtggct ctggccatct accgcagatc gtaagtggac            3948
tcgaccgagc catcccacgc atcaaaagcg cgaataagat ctacaaagtc agcaatcata            4008
```

```
ctcct                                                              4013
```

<210> SEQ ID NO 2
<211> LENGTH: 690
<212> TYPE: PRT
<213> ORGANISM: Aspergillus oryzae

<400> SEQUENCE: 2

```
Met Met His Phe Leu Ser Phe Cys Leu Ser Val Ala Ser Leu Val Ser
-20             -15                 -10                  -5

Tyr Ala Gly Ala Ala Ser Thr Phe Ser Pro Ala Arg Pro Pro Ala Leu
        -1   1              5                  10

Pro Leu Ala Val Lys Ser Pro Tyr Leu Ser Thr Trp Leu Ser Ala Gly
         15                  20                  25

Thr Asp Gly Gly Asn Gly Tyr Leu Ala Gly Gln Trp Pro Thr Phe
     30              35                  40

Trp Phe Gly Gln Val Thr Gly Trp Ala Gly Gln Ile Arg Val Asp Asn
 45              50                  55                      60

Ser Thr Tyr Thr Trp Met Gly Ala Ile Pro Asn Thr Pro Thr Val Asn
                 65                  70                  75

Gln Thr Ser Phe Glu Tyr Thr Ser Thr Ser Val Phe Thr Met Arg
             80              85                  90

Val Gly Asp Met Val Glu Met Lys Val Lys Phe Leu Ser Pro Ile Thr
         95             100                 105

Pro Asp Asp Leu Arg Arg Gln Ser Leu Val Phe Ser Tyr Leu Asp Val
    110                 115                 120

Asp Val Glu Ser Ile Asp Gly Lys Ala His Asp Ile Gln Val Tyr Ala
125             130                 135                     140

Asp Ile Ser Ala Glu Trp Ala Ser Gly Asp Arg Asn Ala Ile Ala Gln
                145                 150                 155

Trp Asp Tyr Gly Val Thr Asp Asp Gly Val Ala Tyr His Lys Val Tyr
                160                 165                 170

Arg Gln Thr Gln Leu Leu Phe Ser Glu Asn Thr Glu Gln Ala Glu Trp
            175                 180                 185

Gly Glu Trp Tyr Trp Ala Thr Asp Gln Asp Gly Leu Ser Tyr Gln
    190                 195                 200

Ser Gly Pro Asp Val Asp Val Arg Gly Ala Phe Ala Lys Asn Gly Lys
205                 210                 215                 220

Leu Ala Asn Ser Asp Asp Lys Asn Tyr Arg Ala Ile Ser Thr Asn Trp
                225                 230                 235

Pro Val Phe Ala Phe Ser Arg Asp Leu Gly Ser Val Lys Thr Ser Ala
                240                 245                 250

Gly Thr Leu Phe Ser Ile Gly Leu Ala Gln Asp Ser Ala Ile Gln Tyr
                255                 260                 265

Ser Gly Lys Pro Glu Gly Thr Thr Val Met Pro Ser Leu Trp Lys Ser
            270                 275                 280

Tyr Phe Ser Thr Ala Thr Ala Leu Glu Phe Phe His His Asp Tyr
285                 290                 295                 300

Ala Ala Ala Ala Ala Leu Ser Lys Asp Leu Asp Asp Arg Ile Ser Lys
                305                 310                 315

Asp Ser Ile Asp Ala Ala Gly Gln Asp Tyr Leu Thr Ile Thr Ser Leu
                320                 325                 330

Thr Val Arg Gln Val Phe Ala Ala Val Gln Leu Thr Gly Thr Pro Glu
            335                 340                 345
```

```
Asp Pro Tyr Ile Phe Met Lys Glu Ile Ser Ser Asn Gly Asn Met Asn
    350                 355                 360

Thr Val Asp Val Ile Phe Pro Ala His Pro Ile Phe Leu Tyr Thr Asn
365                 370                 375                 380

Pro Glu Leu Leu Lys Leu Ile Leu Lys Pro Ile Tyr Glu Ile Gln Glu
                385                 390                 395

Asn Gly Lys Tyr Pro Asn Thr Tyr Ala Met His Asp Ile Gly Thr His
            400                 405                 410

Tyr Pro Asn Ala Thr Gly His Pro Lys Gly Asp Glu Lys Met Pro
        415                 420                 425

Leu Glu Glu Cys Gly Asn Met Val Ile Met Ala Leu Ala Tyr Ala Gln
    430                 435                 440

Lys Ala Lys Asp Asn Asp Tyr Leu Ser Gln His Tyr Pro Ile Leu Asn
445                 450                 455                 460

Lys Trp Thr Thr Tyr Leu Val Glu Asp Ser Ile Tyr Pro Ala Asn Gln
                465                 470                 475

Ile Ser Thr Asp Asp Phe Ala Gly Ser Leu Ala Asn Gln Thr Asn Leu
            480                 485                 490

Ala Leu Lys Gly Ile Ile Gly Ile Gln Ala Met Ala Val Ile Ser Asn
        495                 500                 505

Thr Thr Gly His Pro Asp Asp Ala Ser Asn His Ser Ser Ile Ala Lys
    510                 515                 520

Asp Tyr Ile Ala Arg Trp Gln Thr Leu Gly Val Ala His Asp Ala Asn
525                 530                 535                 540

Pro Pro His Thr Thr Leu Ser Tyr Gly Ala Asn Glu Thr His Gly Leu
                545                 550                 555

Leu Tyr Asn Leu Tyr Ala Asp Arg Glu Leu Gly Leu Asn Leu Val Pro
            560                 565                 570

Gln Ser Val Tyr Asp Met Gln Asn Thr Phe Tyr Pro Thr Val Lys Glu
        575                 580                 585

Lys Tyr Gly Val Pro Leu Asp Thr Arg His Val Tyr Thr Lys Ala Asp
    590                 595                 600

Trp Glu Leu Phe Thr Ala Ala Val Ala Ser Glu Ser Val Arg Asp Met
605                 610                 615                 620

Phe His Gln Ala Leu Ala Thr Trp Ile Asn Glu Thr Pro Thr Asn Arg
                625                 630                 635

Ala Phe Thr Asp Leu Tyr Asp Thr Gln Thr Gly Asn Tyr Pro Ala Gly
            640                 645                 650

Ile Thr Phe Ile Ala Arg Pro Val Met Gly Gly Ala Phe Ala Leu Leu
        655                 660                 665

Ile Leu
    670

<210> SEQ ID NO 3
<211> LENGTH: 17
<212> TYPE: PRT
<213> ORGANISM: Aspergillus oryzae

<400> SEQUENCE: 3

Ala Ser Thr Phe Ser Pro Ala Arg Pro Pro Ala Leu Pro Leu Ala Val
1               5                   10                  15

Lys

<210> SEQ ID NO 4
```

```
<211> LENGTH: 10
<212> TYPE: PRT
<213> ORGANISM: Aspergillus oryzae
<220> FEATURE:
<221> NAME/KEY: MISC_FEATURE
<222> LOCATION: (2)..(2)
<223> OTHER INFORMATION: Xaa = Gly or Pro
<220> FEATURE:
<221> NAME/KEY: MISC_FEATURE
<222> LOCATION: (3)..(3)
<223> OTHER INFORMATION: Xaa = Asn or Val
<220> FEATURE:
<221> NAME/KEY: MISC_FEATURE
<222> LOCATION: (4)..(4)
<223> OTHER INFORMATION: Xaa = Thr or Pro
<220> FEATURE:
<221> NAME/KEY: MISC_FEATURE
<222> LOCATION: (8)..(8)
<223> OTHER INFORMATION: Xaa = Arg or Ser

<400> SEQUENCE: 4

Tyr Xaa Xaa Xaa Tyr Ala Met Xaa Gln Ile
1               5                   10

<210> SEQ ID NO 5
<211> LENGTH: 9
<212> TYPE: PRT
<213> ORGANISM: Aspergillus oryzae
<220> FEATURE:
<221> NAME/KEY: MISC_FEATURE
<222> LOCATION: (4)..(4)
<223> OTHER INFORMATION: Xaa = Thr or Gly
<220> FEATURE:
<221> NAME/KEY: MISC_FEATURE
<222> LOCATION: (8)..(8)
<223> OTHER INFORMATION: Xaa is uncertain

<400> SEQUENCE: 5

Val Gln Tyr Xaa Glu Tyr Asp Xaa Tyr
1               5

<210> SEQ ID NO 6
<211> LENGTH: 14
<212> TYPE: PRT
<213> ORGANISM: Aspergillus oryzae

<400> SEQUENCE: 6

Asp Asn Asp Tyr Leu Ser Gln His Tyr Pro Ile Leu Asn Lys
1               5                   10

<210> SEQ ID NO 7
<211> LENGTH: 15
<212> TYPE: PRT
<213> ORGANISM: Aspergillus oyyzae

<400> SEQUENCE: 7

Trp Thr Ala Tyr Leu Val Gln Asp Thr Ile Tyr Pro Ala Asn Gln
1               5                   10                  15

<210> SEQ ID NO 8
<211> LENGTH: 10
<212> TYPE: PRT
<213> ORGANISM: Aspergillus oryzae

<400> SEQUENCE: 8

Val Leu Leu Gln Ser Ala Ile Glu Gly His
1               5                   10

<210> SEQ ID NO 9
```

```
<211> LENGTH: 10
<212> TYPE: PRT
<213> ORGANISM: Aspergillus oryzae

<400> SEQUENCE: 9

Gly Ile Ile Gly Ile Asn Ala Met Ala Val
1               5                   10

<210> SEQ ID NO 10
<211> LENGTH: 10
<212> TYPE: PRT
<213> ORGANISM: Aspergillus oryzae
<220> FEATURE:
<221> NAME/KEY: MISC_FEATURE
<222> LOCATION: (1)..(1)
<223> OTHER INFORMATION: Xaa is uncertain
<220> FEATURE:
<221> NAME/KEY: MISC_FEATURE
<222> LOCATION: (6)..(6)
<223> OTHER INFORMATION: Xaa is uncertain
<220> FEATURE:
<221> NAME/KEY: MISC_FEATURE
<222> LOCATION: (8)..(8)
<223> OTHER INFORMATION: Xaa is uncertain
<220> FEATURE:
<221> NAME/KEY: MISC_FEATURE
<222> LOCATION: (9)..(9)
<223> OTHER INFORMATION: Xaa is uncertain

<400> SEQUENCE: 10

Xaa Ile Leu Lys Phe Xaa Tyr Xaa Xaa Gln
1               5                   10

<210> SEQ ID NO 11
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 11
taccccaaca cctatgctat gcgcgatatc                                          30

<210> SEQ ID NO 12
<211> LENGTH: 36
<212> TYPE: DNA
<213> ORGANISM: ARTIFICIAL SEQUENCE
<220> FEATURE:
<223> OTHER INFORMATION: SYNTHETIC DNA

<400> SEQUENCE: 12
ttggttcgcc ggataaatag tatcttcgac caagta                                   36

<210> SEQ ID NO 13
<211> LENGTH: 29
<212> TYPE: DNA
<213> ORGANISM: ARTIFICIAL SEQUENCE
<220> FEATURE:
<223> OTHER INFORMATION: SYNTHETIC DNA

<400> SEQUENCE: 13
gatcatgatg catttcctct cgttctgtc                                           29

<210> SEQ ID NO 14
<211> LENGTH: 28
<212> TYPE: DNA
<213> ORGANISM: ARTIFICIAL SEQUENCE
<220> FEATURE:
<223> OTHER INFORMATION: SYNTHETIC DNA
```

-continued

<400> SEQUENCE: 14
gcaaagtcat ccgtagagat ctggttcg                                28

<210> SEQ ID NO 15
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 15
ggcgaaccag atctctacgg atgactttgc                              30

<210> SEQ ID NO 16
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 16
ctgatctaga cctgcaggct c                                       21

<210> SEQ ID NO 17
<211> LENGTH: 2269
<212> TYPE: DNA
<213> ORGANISM: Aspergillus oryzae
<220> FEATURE:
<221> NAME/KEY: CDS
<222> LOCATION: (1)..(2070)
<223> OTHER INFORMATION:
<220> FEATURE:
<221> NAME/KEY: sig_peptide
<222> LOCATION: (1)..(60)
<223> OTHER INFORMATION:
<220> FEATURE:
<221> NAME/KEY: mat_peptide
<222> LOCATION: (61)..()
<223> OTHER INFORMATION:

<400> SEQUENCE: 17

| atg | atg | cat | ttc | ctc | tcg | ttc | tgt | ctg | tcg | gtg | gcc | tcc | ctg | gtg | tct | 48 |
| Met | Met | His | Phe | Leu | Ser | Phe | Cys | Leu | Ser | Val | Ala | Ser | Leu | Val | Ser |  |
| -20 |     |     |     | -15 |     |     |     |     | -10 |     |     |     |     | -5  |     |  |

| tac | gcc | gga | gct | gcg | tca | aca | ttc | tcc | cct | gcg | agg | cca | ccc | gcc | ctg | 96 |
| Tyr | Ala | Gly | Ala | Ala | Ser | Thr | Phe | Ser | Pro | Ala | Arg | Pro | Pro | Ala | Leu |  |
|     |     |     | -1  | 1   |     |     |     | 5   |     |     |     |     | 10  |     |     |  |

| ccc | ttg | gct | gtc | aaa | tcg | ccg | tac | ttg | agc | aca | tgg | ctc | tct | gcg | ggc | 144 |
| Pro | Leu | Ala | Val | Lys | Ser | Pro | Tyr | Leu | Ser | Thr | Trp | Leu | Ser | Ala | Gly |  |
|     |     |     | 15  |     |     |     |     | 20  |     |     |     |     | 25  |     |     |  |

| aca | gat | ggc | ggt | aat | gga | ggg | tac | ctg | gcc | ggc | caa | tgg | cct | acc | ttc | 192 |
| Thr | Asp | Gly | Gly | Asn | Gly | Gly | Tyr | Leu | Ala | Gly | Gln | Trp | Pro | Thr | Phe |  |
|     | 30  |     |     |     |     | 35  |     |     |     |     | 40  |     |     |     |     |  |

| tgg | ttc | ggc | cag | gtg | acc | ggc | tgg | gcg | ggt | cag | atc | cgg | gtc | gat | aat | 240 |
| Trp | Phe | Gly | Gln | Val | Thr | Gly | Trp | Ala | Gly | Gln | Ile | Arg | Val | Asp | Asn |  |
| 45  |     |     |     |     | 50  |     |     |     |     | 55  |     |     |     |     | 60  |  |

| tcg | acc | tac | aca | tgg | atg | ggg | gcg | atc | cct | aac | acc | cct | acg | gtg | aac | 288 |
| Ser | Thr | Tyr | Thr | Trp | Met | Gly | Ala | Ile | Pro | Asn | Thr | Pro | Thr | Val | Asn |  |
|     |     |     |     | 65  |     |     |     |     | 70  |     |     |     |     | 75  |     |  |

| cag | aca | tcc | ttc | gag | tac | acc | tcg | acg | agc | gtg | ttc | acg | atg | cgt | | 336 |
| Gln | Thr | Ser | Phe | Glu | Tyr | Thr | Ser | Thr | Ser | Val | Phe | Thr | Met | Arg |     |  |
|     |     |     | 80  |     |     |     |     | 85  |     |     |     |     | 90  |     |     |  |

| gtt | ggg | gat | atg | gtg | gaa | atg | aaa | gtg | aaa | ttc | ctg | tcc | cct | atc | aca | 384 |
| Val | Gly | Asp | Met | Val | Glu | Met | Lys | Val | Lys | Phe | Leu | Ser | Pro | Ile | Thr |  |

-continued

```
                95                  100                    105
cca gat gat ctc cgg aga cag tcg ctt gtg ttt tcc tat ctg gac gta      432
Pro Asp Asp Leu Arg Arg Gln Ser Leu Val Phe Ser Tyr Leu Asp Val
        110                 115                 120 gat gtc gaa tcg atc gac ggc aaa gcg cat gac ata cag gtg tac gca      480
Asp Val Glu Ser Ile Asp Gly Lys Ala His Asp Ile Gln Val Tyr Ala
125                 130                 135                 140 gac att tca gca gaa tgg gcg tcc ggg gac cga aac gcc att gcg cag      528
Asp Ile Ser Ala Glu Trp Ala Ser Gly Asp Arg Asn Ala Ile Ala Gln
                145                 150                 155 tgg gac tat ggt gtc aca gat gat ggc gtt gcc tat cac aag gtt tac      576
Trp Asp Tyr Gly Val Thr Asp Asp Gly Val Ala Tyr His Lys Val Tyr
        160                 165                 170 cgc caa acg cag ctg ctg ttt tcc gaa aac act gag cag gcc gaa tgg      624
Arg Gln Thr Gln Leu Leu Phe Ser Glu Asn Thr Glu Gln Ala Glu Trp
175                 180                 185 ggc gag tgg tac tgg gcc aca gac gac caa gat ggt ctg agc tac cag      672
Gly Glu Trp Tyr Trp Ala Thr Asp Asp Gln Asp Gly Leu Ser Tyr Gln
                190                 195                 200 tcc gga ccg gat gtt gat gtg cga ggg gca ttc gca aag aac gga aag      720
Ser Gly Pro Asp Val Asp Val Arg Gly Ala Phe Ala Lys Asn Gly Lys
205                 210                 215                 220 ttg gcg aat tcg gat gat aaa aat tat cgt gca atc tcg acc aat tgg      768
Leu Ala Asn Ser Asp Asp Lys Asn Tyr Arg Ala Ile Ser Thr Asn Trp
                225                 230                 235 ccc gtg ttt gcc ttc tcc cgc gat ctt ggc tcg gtg aag acg tct gct      816
Pro Val Phe Ala Phe Ser Arg Asp Leu Gly Ser Val Lys Thr Ser Ala
        240                 245                 250 ggc acg tta ttc tcc att ggc ctt gcg cag gac agt gcc ata cag tac      864
Gly Thr Leu Phe Ser Ile Gly Leu Ala Gln Asp Ser Ala Ile Gln Tyr
        255                 260                 265 agt ggg aaa cct gaa ggg aca act gtg atg cct tca ctc tgg aag agc      912
Ser Gly Lys Pro Glu Gly Thr Thr Val Met Pro Ser Leu Trp Lys Ser
270                 275                 280 tac ttc agc act gcg act gct gcg ctt gag ttc ttc cat cat gat tat      960
Tyr Phe Ser Thr Ala Thr Ala Ala Leu Glu Phe Phe His His Asp Tyr
285                 290                 295                 300 gct gct gca gct gca cta tcg aag gat ctc gat gac cgg ata tcc aag     1008
Ala Ala Ala Ala Ala Leu Ser Lys Asp Leu Asp Asp Arg Ile Ser Lys
                305                 310                 315 gat tcc att gat gcc gct ggc cag gac tac ctg aca atc acc tcc ctc     1056
Asp Ser Ile Asp Ala Ala Gly Gln Asp Tyr Leu Thr Ile Thr Ser Leu
        320                 325                 330 acg gtc cgt caa gtc ttt gct gcc gtg caa ttg acc ggc acg ccc gag     1104
Thr Val Arg Gln Val Phe Ala Ala Val Gln Leu Thr Gly Thr Pro Glu
        335                 340                 345 gac ccc tac atc ttc atg aag gag atc tcg tcc aat ggc aac atg aac     1152
Asp Pro Tyr Ile Phe Met Lys Glu Ile Ser Ser Asn Gly Asn Met Asn
350                 355                 360 act gtg gac gtc atc ttc ccc gct cac ccg atc ttt ttg tac acc aat     1200
Thr Val Asp Val Ile Phe Pro Ala His Pro Ile Phe Leu Tyr Thr Asn
365                 370                 375                 380 ccc gag ctc ctc aaa ctg att ctg aag cca atc tat gag att caa gag     1248
Pro Glu Leu Leu Lys Leu Ile Leu Lys Pro Ile Tyr Glu Ile Gln Glu
                385                 390                 395 aac gga aag tat ccc aac aca tac gcc atg cac gat att gga acc cac     1296
Asn Gly Lys Tyr Pro Asn Thr Tyr Ala Met His Asp Ile Gly Thr His
                400                 405                 410 tac ccg aac gcc acg ggc cat cct aag ggc gac gac gag aaa atg cca     1344
```

-continued

```
                Tyr Pro Asn Ala Thr Gly His Pro Lys Gly Asp Asp Glu Lys Met Pro
                        415                 420                 425 ctc gag gag tgt gga aac atg gtt atc atg gcc ctt gcc tac gcc cag       1392
Leu Glu Glu Cys Gly Asn Met Val Ile Met Ala Leu Ala Tyr Ala Gln
        430                 435                 440 aag gcc aag gac aac gac tat ctt tca cag cac tat ccc atc ctc aac       1440
Lys Ala Lys Asp Asn Asp Tyr Leu Ser Gln His Tyr Pro Ile Leu Asn
445                 450                 455                 460 aaa tgg aca aca tac ctc gtc gag gat tct att tac ccg gcg aac cag       1488
Lys Trp Thr Thr Tyr Leu Val Glu Asp Ser Ile Tyr Pro Ala Asn Gln
                465                 470                 475 atc tct acg gat gac ttt gct ggc tcg cta gca aac cag acc aac ctg       1536
Ile Ser Thr Asp Asp Phe Ala Gly Ser Leu Ala Asn Gln Thr Asn Leu
            480                 485                 490 gca ttg aag gga atc att gga atc cag gca atg gct gtg atc agc aat       1584
Ala Leu Lys Gly Ile Ile Gly Ile Gln Ala Met Ala Val Ile Ser Asn
        495                 500                 505 acg aca gga cac ccg gac gat gcc tcc aac cac tcc agc att gcc aag       1632
Thr Thr Gly His Pro Asp Asp Ala Ser Asn His Ser Ser Ile Ala Lys
    510                 515                 520 gac tac atc gcg agg tgg cag aca cta ggc gta gct cac gat gcc aat       1680
Asp Tyr Ile Ala Arg Trp Gln Thr Leu Gly Val Ala His Asp Ala Asn
525                 530                 535                 540 cct ccg cat aca acg ctg tcg tac gga gcg aac gag act cat ggg ctt       1728
Pro Pro His Thr Thr Leu Ser Tyr Gly Ala Asn Glu Thr His Gly Leu
                545                 550                 555 ctg tac aat ctg tat gcg gat cgt gaa ttg ggc ttg aac ttg gtt cct       1776
Leu Tyr Asn Leu Tyr Ala Asp Arg Glu Leu Gly Leu Asn Leu Val Pro
            560                 565                 570 cag tcg gtc tat gac atg caa aac acc ttc tat ccg acg gtg aag gag       1824
Gln Ser Val Tyr Asp Met Gln Asn Thr Phe Tyr Pro Thr Val Lys Glu
        575                 580                 585 aag tat gga gtg ccg ctc gat act cga cac gtg tac act aag gcg gat       1872
Lys Tyr Gly Val Pro Leu Asp Thr Arg His Val Tyr Thr Lys Ala Asp
    590                 595                 600 tgg gag ctt ttc aca gct gcg gtt gcg tcg gag agt gtc cga gac atg       1920
Trp Glu Leu Phe Thr Ala Ala Val Ala Ser Glu Ser Val Arg Asp Met
605                 610                 615                 620 ttc cac cag gcg ctc gcg acg tgg atc aac gag aca ccg acc aac cgt       1968
Phe His Gln Ala Leu Ala Thr Trp Ile Asn Glu Thr Pro Thr Asn Arg
                625                 630                 635 gcc ttt acg gat ctc tat gat acc caa act gga aat tat ccg gcg ggc       2016
Ala Phe Thr Asp Leu Tyr Asp Thr Gln Thr Gly Asn Tyr Pro Ala Gly
            640                 645                 650 att acg ttc att gcg cgg ccc gtc atg ggt ggt gcc ttt gcg ttg tta       2064
Ile Thr Phe Ile Ala Arg Pro Val Met Gly Gly Ala Phe Ala Leu Leu
        655                 660                 665 att ctc tagagtcgtt tcattgtata ttgattttat tcgcttctgg gcgcgagtgg        2120
Ile Leu
    670 agacacttgc ttactttgtt tccaatttta ttattaccgt ggctatggga ccagattgac     2180 cgttgttaat agcgtacctc atacatagca ttttattct gcaaaaaaaa aaaaaaaaa       2240 aaaaaaaaaa aaaaaaaaaa aaaaaaaa                                        2269

<210> SEQ ID NO 18
<211> LENGTH: 690
<212> TYPE: PRT
<213> ORGANISM: Aspergillus oryzae
```

<400> SEQUENCE: 18

```
Met Met His Phe Leu Ser Phe Cys Leu Ser Val Ala Ser Leu Val Ser
-20                 -15                 -10                  -5
Tyr Ala Gly Ala Ala Ser Thr Phe Ser Pro Ala Arg Pro Pro Ala Leu
            -1   1              5                  10
Pro Leu Ala Val Lys Ser Pro Tyr Leu Ser Thr Trp Leu Ser Ala Gly
             15                 20                  25
Thr Asp Gly Gly Asn Gly Gly Tyr Leu Ala Gly Gln Trp Pro Thr Phe
        30                  35                  40
Trp Phe Gly Gln Val Thr Gly Trp Ala Gly Gln Ile Arg Val Asp Asn
45                   50                  55                  60
Ser Thr Tyr Thr Trp Met Gly Ala Ile Pro Asn Thr Pro Thr Val Asn
                65                  70                  75
Gln Thr Ser Phe Glu Tyr Thr Ser Thr Ser Ser Val Phe Thr Met Arg
                80                  85                  90
Val Gly Asp Met Val Glu Met Lys Val Lys Phe Leu Ser Pro Ile Thr
             95                 100                 105
Pro Asp Asp Leu Arg Arg Gln Ser Leu Val Phe Ser Tyr Leu Asp Val
    110                 115                 120
Asp Val Glu Ser Ile Asp Gly Lys Ala His Asp Ile Gln Val Tyr Ala
125                 130                 135                 140
Asp Ile Ser Ala Glu Trp Ala Ser Gly Asp Arg Asn Ala Ile Ala Gln
                145                 150                 155
Trp Asp Tyr Gly Val Thr Asp Asp Gly Val Ala Tyr His Lys Val Tyr
                160                 165                 170
Arg Gln Thr Gln Leu Leu Phe Ser Glu Asn Thr Glu Gln Ala Glu Trp
                175                 180                 185
Gly Glu Trp Tyr Trp Ala Thr Asp Asp Gln Asp Gly Leu Ser Tyr Gln
    190                 195                 200
Ser Gly Pro Asp Val Asp Val Arg Gly Ala Phe Ala Lys Asn Gly Lys
205                 210                 215                 220
Leu Ala Asn Ser Asp Asp Lys Asn Tyr Arg Ala Ile Ser Thr Asn Trp
                225                 230                 235
Pro Val Phe Ala Phe Ser Arg Asp Leu Gly Ser Val Lys Thr Ser Ala
                240                 245                 250
Gly Thr Leu Phe Ser Ile Gly Leu Ala Gln Asp Ser Ala Ile Gln Tyr
                255                 260                 265
Ser Gly Lys Pro Glu Gly Thr Thr Val Met Pro Ser Leu Trp Lys Ser
    270                 275                 280
Tyr Phe Ser Thr Ala Thr Ala Ala Leu Glu Phe Phe His His Asp Tyr
285                 290                 295                 300
Ala Ala Ala Ala Ala Leu Ser Lys Asp Leu Asp Asp Arg Ile Ser Lys
                305                 310                 315
Asp Ser Ile Asp Ala Ala Gly Gln Asp Tyr Leu Thr Ile Thr Ser Leu
                320                 325                 330
Thr Val Arg Gln Val Phe Ala Ala Val Gln Leu Thr Gly Thr Pro Glu
                335                 340                 345
Asp Pro Tyr Ile Phe Met Lys Glu Ile Ser Ser Asn Gly Asn Met Asn
    350                 355                 360
Thr Val Asp Val Ile Phe Pro Ala His Pro Ile Phe Leu Tyr Thr Asn
365                 370                 375                 380
Pro Glu Leu Leu Lys Leu Ile Leu Lys Pro Ile Tyr Glu Ile Gln Glu
                385                 390                 395
```

Asn Gly Lys Tyr Pro Asn Thr Tyr Ala Met His Asp Ile Gly Thr His
            400                 405                 410
Tyr Pro Asn Ala Thr Gly His Pro Lys Gly Asp Asp Glu Lys Met Pro
        415                 420                 425
Leu Glu Glu Cys Gly Asn Met Val Ile Met Ala Leu Ala Tyr Ala Gln
    430                 435                 440
Lys Ala Lys Asp Asn Asp Tyr Leu Ser Gln His Tyr Pro Ile Leu Asn
445                 450                 455                 460
Lys Trp Thr Thr Tyr Leu Val Glu Asp Ser Ile Tyr Pro Ala Asn Gln
            465                 470                 475
Ile Ser Thr Asp Asp Phe Ala Gly Ser Leu Ala Asn Gln Thr Asn Leu
        480                 485                 490
Ala Leu Lys Gly Ile Ile Gly Ile Gln Ala Met Ala Val Ile Ser Asn
    495                 500                 505
Thr Thr Gly His Pro Asp Asp Ala Ser Asn His Ser Ser Ile Ala Lys
510                 515                 520
Asp Tyr Ile Ala Arg Trp Gln Thr Leu Gly Val Ala His Asp Ala Asn
525                 530                 535                 540
Pro Pro His Thr Thr Leu Ser Tyr Gly Ala Asn Glu Thr His Gly Leu
            545                 550                 555
Leu Tyr Asn Leu Tyr Ala Asp Arg Glu Leu Gly Leu Asn Leu Val Pro
        560                 565                 570
Gln Ser Val Tyr Asp Met Gln Asn Thr Phe Tyr Pro Thr Val Lys Glu
    575                 580                 585
Lys Tyr Gly Val Pro Leu Asp Thr Arg His Val Tyr Thr Lys Ala Asp
590                 595                 600
Trp Glu Leu Phe Thr Ala Ala Val Ala Ser Glu Ser Val Arg Asp Met
605                 610                 615                 620
Phe His Gln Ala Leu Ala Thr Trp Ile Asn Glu Thr Pro Thr Asn Arg
            625                 630                 635
Ala Phe Thr Asp Leu Tyr Asp Thr Gln Thr Gly Asn Tyr Pro Ala Gly
        640                 645                 650
Ile Thr Phe Ile Ala Arg Pro Val Met Gly Gly Ala Phe Ala Leu Leu
        655                 660                 665
Ile Leu
    670

<210> SEQ ID NO 19
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 19
gacgaccaag atggtctgag ctaccagt                                    28

<210> SEQ ID NO 20
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 20
gcaaagtcat ccgtagagat ctggttcgcc                                  30

```
<210> SEQ ID NO 21
<211> LENGTH: 6191
<212> TYPE: DNA
<213> ORGANISM: Aspergillus nidulans
<220> FEATURE:
<221> NAME/KEY: CDS
<222> LOCATION: (1807)..(2000)
<223> OTHER INFORMATION:
<220> FEATURE:
<221> NAME/KEY: CDS
<222> LOCATION: (2061)..(2353)
<223> OTHER INFORMATION:
<220> FEATURE:
<221> NAME/KEY: CDS
<222> LOCATION: (2412)..(2854)
<223> OTHER INFORMATION:
<220> FEATURE:
<221> NAME/KEY: CDS
<222> LOCATION: (2915)..(3498)
<223> OTHER INFORMATION:
<220> FEATURE:
<221> NAME/KEY: CDS
<222> LOCATION: (3554)..(3756)
<223> OTHER INFORMATION:
<220> FEATURE:
<221> NAME/KEY: CDS
<222> LOCATION: (3806)..(3949)
<223> OTHER INFORMATION:
<220> FEATURE:
<221> NAME/KEY: CDS
<222> LOCATION: (3996)..(4131)
<223> OTHER INFORMATION:
<220> FEATURE:
<221> NAME/KEY: CDS
<222> LOCATION: (4180)..(4246)
<223> OTHER INFORMATION:
<220> FEATURE:
<221> NAME/KEY: Intron
<222> LOCATION: (2001)..(2060)
<223> OTHER INFORMATION:
<220> FEATURE:
<221> NAME/KEY: Intron
<222> LOCATION: (2354)..(2411)
<223> OTHER INFORMATION:
<220> FEATURE:
<221> NAME/KEY: Intron
<222> LOCATION: (2855)..(2914)
<223> OTHER INFORMATION:
<220> FEATURE:
<221> NAME/KEY: Intron
<222> LOCATION: (3499)..(3553)
<223> OTHER INFORMATION:
<220> FEATURE:
<221> NAME/KEY: Intron
<222> LOCATION: (3757)..(3805)
<223> OTHER INFORMATION:
<220> FEATURE:
<221> NAME/KEY: Intron
<222> LOCATION: (3950)..(3995)
<223> OTHER INFORMATION:
<220> FEATURE:
<221> NAME/KEY: Intron
<222> LOCATION: (4132)..(4179)
<223> OTHER INFORMATION:
<220> FEATURE:
<221> NAME/KEY: sig_peptide
<222> LOCATION: (1807)..(1863)
<223> OTHER INFORMATION:
<220> FEATURE:
<221> NAME/KEY: mat_peptide
<222> LOCATION: (1864)..()
<223> OTHER INFORMATION:

<400> SEQUENCE: 21
gatatccaat gtctagggcg tacggcattc tgaaatgatc cgtgtactgc acgaatactc      60
catactacgt accacaagat tgaacaccct attatcaaac ttcgagagtc tgctgggcgt     120
```

-continued

```
ataactgctg ggtggcgaac cgcgaaatta ttataccttta ggaggctccg gtctcaacgt      180
gtaagcacta acgaaccctg tccgctatgc tgtgcaagtc atcagcacct cagcttgcag      240
cgttcgccta cttaatccgt aacccgagga ccggaccggc aagactcgat tgtcccatgt      300
gctctgtacc tgcgtggatg cactcccag catctgctgt gccaaacgaa gcggatcgct       360
ccaagcctgt tcgtccgaca acattcgcct tcacggcgag gccgaaacgg atctctgtgt      420
gtccatagcc atttcagcct tctgtttatg cgttatatgt gctgaggata tacgccgagc      480
cgcagggggg caagtagtgg gttaatgacg ggacctccgc atttctcttt gaatctggct      540
gttagcgtgt cacttggctc gggttgggct gggtcatgca cggatctgca tcaagtcagt      600
ctcttgtgat gtacgctgat ccggtgatgt acatatgagg ggtagaagat actcggggca      660
gacactgact ttgtatggtg ggaacgatgt cacacaatgc aggcacagac atccagccaa      720 caccttgta cagagtatgc aaacaatgag ttggccagtc ggttgccagg attctcgttg       780
cagcgcagga cagccaagag aagaaccaga gagatgaggg caatatctaa tccagtctct      840
tgcatggtcc tctcccgcgt cattccgtac tggaatgtga ggggccgtat gtggaaatat      900
tgcttgggat gacaaagggc gtgaagagtg aagggtttct tcaagtgctg gacggaagag      960
tagggaggac tttgagcatg gcactttcct cttagggtac tctccagtcc cacgttttcg     1020
cctcgctcct cgctctccaa ctcctctatt ttcccacaaa acacttctct ccttcgtatg     1080
ctcctgctct gaatcagctt ggaaccctct cataaccctc cgggggggg gcccgcgttc      1140 gttgataacc catgctacca tggcaaatga ccttactgac ggcgtaacag atctacttcg     1200
cttggtcgaa cttcatgctt atttctaagc ttggttacta taggctcccg cgccgttttg     1260
ggttgatcct ccctggtcag tcgtatttca accgttctg cagagtagcg gtggagcata      1320
caagaaatac tcatgattga ttcttatagg agcggatctc ctctgtggag tatacaccca     1380
atttcaaacc cctgttccct tcgctcgatt ggctattttc tttcgttttc catgtgtata     1440
gtggcgacgg catgcgctgg tgcagataga atgatcggtc agacgacatt attcgagaaa     1500
gttatgccta tgcatgtgca gatgcttctg cctcgattcg aaagagtcta gacagggctt     1560
tccacatgct ggcaccaaga gtccactcct agaattctat aaagaaacct tcatccgcct     1620
ggaatgcaag atatatccac tgtacagccg tgcctagcat tccgctgccc attcccaagg     1680
cccacattgc tgctcgatta tttgtcactc cttgaaattg cttcataatt ctcctgttgt     1740
tgagtctttt aaacgggcc tattagaagg gggttgcacg gctgaggatc acctacccag      1800
``` atcaat atg cgt act ttt cta cta ggc atc ctg tgc gca ccc ctg gct    1848
        Met Arg Thr Phe Leu Leu Gly Ile Leu Cys Ala Pro Leu Ala
                    -15                 -10 atc ctt aca gga gcc gca tcg act ttt tct cca gca cgc cct ccg gct    1896
Ile Leu Thr Gly Ala Ala Ser Thr Phe Ser Pro Ala Arg Pro Pro Ala
-5              -1  1               5                   10 ctt cct cta gcg gtc aaa tct ccg tac ttg agt act tgg ctg ccg gcg    1944
Leu Pro Leu Ala Val Lys Ser Pro Tyr Leu Ser Thr Trp Leu Pro Ala
            15                  20                  25 ggg aaa gac ggc ggc aat gga ggc tac ctt gca ggg gaa tgg cca gcg    1992
Gly Lys Asp Gly Gly Asn Gly Gly Tyr Leu Ala Gly Glu Trp Pro Ala
        30                  35                  40 ttc tgg ga   gtgagtgcta tgaacctggc ataacaatta cagagagctg            2040
Phe Trp Glu
        45 aaaaagaatc attgttatag a ggc caa ata aca gga tgg gct ggc ctt att    2091
                        Gly Gln Ile Thr Gly Trp Ala Gly Leu Ile

```
                                  50                          55
cgt gtg gat ggc cag gtc tat aca tgg atg ggc ctt cca ggc tca gcc        2139
Arg Val Asp Gly Gln Val Tyr Thr Trp Met Gly Leu Pro Gly Ser Ala
            60                  65                  70 act gtg aac cag act gcg tat gag tac act tca acg aag agc att ttc        2187
Thr Val Asn Gln Thr Ala Tyr Glu Tyr Thr Ser Thr Lys Ser Ile Phe
        75                  80                  85 acc atg cat att ggt gat atg gta gag atg aag ata acc ttc ctt tca        2235
Thr Met His Ile Gly Asp Met Val Glu Met Lys Ile Thr Phe Leu Ser
    90                  95                  100 cca att aca ccg aat gat ctt cga cgg cag tcc cta gtg ttt tcg tat        2283
Pro Ile Thr Pro Asn Asp Leu Arg Arg Gln Ser Leu Val Phe Ser Tyr
105                 110                 115                 120 ctt gac gtg agt gtc acc tca ctc gac ggc cag tcc cac agt gta cag        2331
Leu Asp Val Ser Val Thr Ser Leu Asp Gly Gln Ser His Ser Val Gln
                125                 130                 135 gtg tac gct gac ata tca gct g gtgagtttac ctggacatac ttcagccaag         2383
Val Tyr Ala Asp Ile Ser Ala
                140 tgaaaaacca ttattgattg ttccctag aa  ttt gcg tct ggc gac cgt tcc         2434
                                   Phe Ala Ser Gly Asp Arg Ser
                                       145                 150 gcc ata gca caa tgg aac tat ggt gtt acc agt gac ggc gta gcc tat        2482
Ala Ile Ala Gln Trp Asn Tyr Gly Val Thr Ser Asp Gly Val Ala Tyr
            155                 160                 165 cat aag atc tat cgc cag acg ccg ctc cta ttc tct gag cat aga gac        2530
His Lys Ile Tyr Arg Gln Thr Pro Leu Leu Phe Ser Glu His Arg Asp
        170                 175                 180 caa gct gaa tgg ggt gat tgg tac tgg gca act gac aat gta gca gga        2578
Gln Ala Glu Trp Gly Asp Trp Tyr Trp Ala Thr Asp Asn Val Ala Gly
    185                 190                 195 ctc act tac cag gct ggt cca gat gtt gat gtc cgg gaa gct ttt gcg        2626
Leu Thr Tyr Gln Ala Gly Pro Asp Val Asp Val Arg Glu Ala Phe Ala
200                 205                 210                 215 cgc aat gga aag cta acc aat aac aac gac gtc aac tac aga gct atc        2674
Arg Asn Gly Lys Leu Thr Asn Asn Asn Asp Val Asn Tyr Arg Ala Ile
                220                 225                 230 tcc aac aac tgg ccg gtg ttt ggt ttt gcc cat gac ctt ggg tct atc        2722
Ser Asn Asn Trp Pro Val Phe Gly Phe Ala His Asp Leu Gly Ser Ile
            235                 240                 245 agc tct tct act aag gtg ctt ttc tca ata ggg cta acc cag cga gag        2770
Ser Ser Ser Thr Lys Val Leu Phe Ser Ile Gly Leu Thr Gln Arg Glu
        250                 255                 260 gca atc cag tat agc ggg aac tct tcc acc ctt tct cct ttg cct gct        2818
Ala Ile Gln Tyr Ser Gly Asn Ser Ser Thr Leu Ser Pro Leu Pro Ala
    265                 270                 275 ctg tgg acg agc tat ttc agc act gcc ttg gat gcc gtgagtgctc             2864
Leu Trp Thr Ser Tyr Phe Ser Thr Ala Leu Asp Ala
280                 285                 290 cccgtgtaga agctagacac cctgggactt actcaaaaac cctatttag ctt gac          2920
                                                            Leu Asp ttc ttc cac cat gat tat cag aag tca aac tct ctt tct tca gat ctt        2968
Phe Phe His His Asp Tyr Gln Lys Ser Asn Ser Leu Ser Ser Asp Leu
        295                 300                 305 gat cgg cga att gca caa gat tcc gtt gcc gct gcc ggt cac gac tac        3016
Asp Arg Arg Ile Ala Gln Asp Ser Val Ala Ala Ala Gly His Asp Tyr
310                 315                 320                 325 ctt acc att aca tcc ctc agc att cgt caa gct ttc gct gca acc cag        3064
Leu Thr Ile Thr Ser Leu Ser Ile Arg Gln Ala Phe Ala Ala Thr Gln
```

```
                330                 335                 340
ctg tgt ggg cca gca aat gat ccg tat ctc ttt atg aaa gaa atc tcc    3112
Leu Cys Gly Pro Ala Asn Asp Pro Tyr Leu Phe Met Lys Glu Ile Ser
            345                 350                 355 tcc aac ggc aac atg aac acg gta gat gtg atc ttc cct gct cat ccc    3160
Ser Asn Gly Asn Met Asn Thr Val Asp Val Ile Phe Pro Ala His Pro
        360                 365                 370 gtc ttc tta tac aca aac cca gca ctg ctt aaa tat ctc ctg cgc cca    3208
Val Phe Leu Tyr Thr Asn Pro Ala Leu Leu Lys Tyr Leu Leu Arg Pro
    375                 380                 385 cat ttg gag atc cag gag tct gga aat tac ccc aac tcc tat gct atg    3256
His Leu Glu Ile Gln Glu Ser Gly Asn Tyr Pro Asn Ser Tyr Ala Met
390                 395                 400                 405 cat gat atc ggt gct cat tac cct aac gct aca ggc cat ccg gat ggc    3304
His Asp Ile Gly Ala His Tyr Pro Asn Ala Thr Gly His Pro Asp Gly
                410                 415                 420 aat gac gag cca atg ccg ttg gag gag tgc ggt aat atg gtg atc atg    3352
Asn Asp Glu Pro Met Pro Leu Glu Glu Cys Gly Asn Met Val Ile Met
            425                 430                 435 gct cta gca tat gcg cag aag gcc ggg gac aca gcg tac ctg gaa agc    3400
Ala Leu Ala Tyr Ala Gln Lys Ala Gly Asp Thr Ala Tyr Leu Glu Ser
        440                 445                 450 cac tac aca ata ctg aga cgt tgg acg gac tac ttg atc gaa gat tct    3448
His Tyr Thr Ile Leu Arg Arg Trp Thr Asp Tyr Leu Ile Glu Asp Ser
    455                 460                 465 ctt tat ccg gcg aac caa ata tcg aca gat gat ttc gca ggt cca ttg    3496
Leu Tyr Pro Ala Asn Gln Ile Ser Thr Asp Asp Phe Ala Gly Pro Leu
470                 475                 480                 485 gc  gtacgtccct actggcgtat aggtgcttct caaaccaaac taatggcgtc tctag    3553
Ala a aat caa acc aac ctc gcc ctg aag gga atc atc ggt atc gag gcc atg  3602
  Asn Gln Thr Asn Leu Ala Leu Lys Gly Ile Ile Gly Ile Glu Ala Met
            490                 495                 500 tct gtc atc gct agc ctg aca gga gac tct gat gat aag atg aat ctc    3650
Ser Val Ile Ala Ser Leu Thr Gly Asp Ser Asp Asp Lys Met Asn Leu
        505                 510                 515 acc aat tac gcc cac gat tac atc gaa aaa tgg ctg att ttg gga att    3698
Thr Asn Tyr Ala His Asp Tyr Ile Glu Lys Trp Leu Ile Leu Gly Ile
    520                 525                 530 gca cgt aac aca acg tat ccg cat aca aca ttg tcg tac gga tca aac    3746
Ala Arg Asn Thr Thr Tyr Pro His Thr Thr Leu Ser Tyr Gly Ser Asn
535                 540                 545                 550 gag tct cat g gtttgtgtac tcctcactgt gatgcttggc caatactgat           3796
Glu Ser His tgttccaag ga   ctc ctg tac aac ctt tac gca gat cgc gag cta ggc ttg  3846
               Gly Leu Leu Tyr Asn Leu Tyr Ala Asp Arg Glu Leu Gly Leu
                   555                 560                 565 aac ctg gtc ccg caa tct gtg tat gac atg cag agc aac ttc tac ccg    3894
Asn Leu Val Pro Gln Ser Val Tyr Asp Met Gln Ser Asn Phe Tyr Pro
        570                 575                 580 aca atc aag ggt caa tac gga gtg cca ctg gat acc cgc cat caa tac    3942
Thr Ile Lys Gly Gln Tyr Gly Val Pro Leu Asp Thr Arg His Gln Tyr
    585                 590                 595 acg aaa g gtatgtggcc atctactcgt cgcggctgta taattgacgg tctcag gt    3997
Thr Lys                                                      Gly
600 gat tgg gag ctc ttc acg gcg gca gtc gca tca gta agc aca cga gac    4045
Asp Trp Glu Leu Phe Thr Ala Ala Val Ala Ser Val Ser Thr Arg Asp
        605                 610                 615
```

-continued

```
atg ttc atc aaa cta ctt gcc cag tgg ata aac gag acg cca acg aac     4093
Met Phe Ile Lys Leu Leu Ala Gln Trp Ile Asn Glu Thr Pro Thr Asn
    620                 625                 630 cgt cca ctt acg gat ctc tat gac act gta acc gga ga gtaagtgtac       4141
Arg Pro Leu Thr Asp Leu Tyr Asp Thr Val Thr Gly Asp
635                 640                 645 ctacctaaac ctaggagacg ctttgctgat tcactcag c tac cca ccg gta gtt     4195
                                            Tyr Pro Pro Val Val
                                                            650 ttc atc gct cga cct gtc atg ggc gcg gca ttc act ttg ttg ctt ctc     4243
Phe Ile Ala Arg Pro Val Met Gly Ala Ala Phe Thr Leu Leu Leu Leu
            655                 660                 665 gac tgaaattctt tccaggtaca tacatgcttt atcaggacaa aagagcggct          4296
Asp aggcggtcca ttcccagtat ttgtgttaga tgtgatatat atggtcgtgt ttaagttgtg   4356
taatattgtg tggtagtata tagcatcagt tatagccttt ttcaatccct ctgggtagct   4416
gaaagtgatg tactatgaat gcagatctgt agagcttgca ttgatactag tcaacatatt   4476
catagtgtta cataggcaag acgacgagaa ccaatgcagt cttttgcttc tgcatttctt   4536
ccgttaaacc gaatttatac cgtcatcaga ttatcgcgtc agttgtctag tactaacctt   4596
gtacctcaaa ggtctgaggt ttgttgttcc gcagcgtccc atgcatcaaa ggcccggatc   4656
agatctgtga tacttagcta cccagctcgt gcaacgatga agaagaccta ccataataca   4716
gcatcatcgc ctcgaggtga gcatcaatgc caactctttc atccacagtg tggatattca   4776
acgcacggcc ctcgcgcgcg ggactccagc ggtaaatgtt tggcgatagg ttccagtaaa   4836
gcctggtatc cgtgttgccg gtggtgatgt ccccaccaac aacgacagtt ttgcctttca   4896
gacttggaac agactcgaag accgagcggg cgacaccggc aaaccgtgcc caaacgggac   4956
ttgtatcgat atcagtaggg ctaacggggg ctggctcgag aggagaattt agggtcgaga   5016
gcgtgagatg accactgctt gccacttcac tgctgatctc gtccttgttg gtatccaaga   5076
atctggacca ggtcaaattg aacttctcta caatgggctc tatgatcttc tccgctcggt   5136
cttggagcat cttcggggtt tggtgcaatg cgatgcgata attcacgaca gcggtgatct   5196
tttccggaag cgcgttgctc tttatgcctc cattgaatat atccgctgcc tgggacgact   5256
ggagagtgaa tcgaacgctt tctccacgag acctagcaat tgcttcggcc gttgctgcct   5316
gatcatccga gtcaagcgca gaagcaagcc agtcctccac atattcagga gaatggcgga   5376
cctggcactc aaacactcgg cgagaagggt gattagaccc taaaatgggc gtgaaaatgt   5436
caagctcagt attctctagc ttgtaaataa tttccgacat tatgccgacc ccggtatgtc   5496
tgggcggaac ggaactatgg ccaccaggga cagcgagggt aaggacgatc gtgacggcgc   5556
ctttctcgcc aacatccggg agcgcgtaaa tcacactctc gtcctcaaat tcctctccag   5616
cggaagataa cgatgagcga agggtggtga taccgccacc tccttcgtca aggatgaatt   5676
ctactccatc tttcccatat ctttcctcca gaaccggagc gattcgcgca gcaccaatat   5736
acccttgtgc ctcctcgtcg aatccaaacg ccaggacaat cggtcgagat ggcgtccagt   5796
tctgagatag gagatcctcg gctacagaga gaagaccgat aaggccgttt ttgcagtcgc   5856
tgcttcctcg tccccagaga aactcgccat caaaataccc tgagaaggga ggatgcgtcc   5916
agtctgaggc atcgttaata gggaccacat cttgatgagc cgtaaagaga aggggctttc   5976
tcttttctac agtttccgag ggaggttcaa gtgttattat aagattgaag cggttgacgt   6036
gctcgatctt ggctttggag tagctgtctc aggttagttt tgggaagaga gatcctgagc   6096
```

```
tgggaaggat acgcgggtga cgcgagggtc attgaagtaa ggaggaaaag ggtaggtgag      6156
ctcacacaag aggaaagagc ccagcaagaa gctta                                 6191
```

<210> SEQ ID NO 22
<211> LENGTH: 688
<212> TYPE: PRT
<213> ORGANISM: Aspergillus nidulans

<400> SEQUENCE: 22

```
Met Arg Thr Phe Leu Leu Gly Ile Leu Cys Ala Pro Leu Ala Ile Leu
            -15                 -10                  -5

Thr Gly Ala Ala Ser Thr Phe Ser Pro Ala Arg Pro Pro Ala Leu Pro
         -1   1               5                  10

Leu Ala Val Lys Ser Pro Tyr Leu Ser Thr Trp Leu Pro Ala Gly Lys
             15                  20                  25

Asp Gly Gly Asn Gly Gly Tyr Leu Ala Gly Glu Trp Pro Ala Phe Trp
 30                  35                  40                  45

Glu Gly Gln Ile Thr Gly Trp Ala Gly Leu Ile Arg Val Asp Gly Gln
                 50                  55                  60

Val Tyr Thr Trp Met Gly Leu Pro Gly Ser Ala Thr Val Asn Gln Thr
                     65                  70                  75

Ala Tyr Glu Tyr Thr Ser Thr Lys Ser Ile Phe Thr Met His Ile Gly
             80                  85                  90

Asp Met Val Glu Met Lys Ile Thr Phe Leu Ser Pro Ile Thr Pro Asn
 95                 100                 105

Asp Leu Arg Arg Gln Ser Leu Val Phe Ser Tyr Leu Asp Val Ser Val
110                 115                 120                 125

Thr Ser Leu Asp Gly Gln Ser His Ser Val Gln Val Tyr Ala Asp Ile
                130                 135                 140

Ser Ala Glu Phe Ala Ser Gly Asp Arg Ser Ala Ile Ala Gln Trp Asn
                145                 150                 155

Tyr Gly Val Thr Ser Asp Gly Val Ala Tyr His Lys Ile Tyr Arg Gln
            160                 165                 170

Thr Pro Leu Leu Phe Ser Glu His Arg Asp Gln Ala Glu Trp Gly Asp
        175                 180                 185

Trp Tyr Trp Ala Thr Asp Asn Val Ala Gly Leu Thr Tyr Gln Ala Gly
190                 195                 200                 205

Pro Asp Val Asp Val Arg Glu Ala Phe Ala Arg Asn Gly Lys Leu Thr
                210                 215                 220

Asn Asn Asn Asp Val Asn Tyr Arg Ala Ile Ser Asn Asn Trp Pro Val
            225                 230                 235

Phe Gly Phe Ala His Asp Leu Gly Ser Ile Ser Ser Thr Lys Val
        240                 245                 250

Leu Phe Ser Ile Gly Leu Thr Gln Arg Glu Ala Ile Gln Tyr Ser Gly
    255                 260                 265

Asn Ser Ser Thr Leu Ser Pro Leu Pro Ala Leu Trp Thr Ser Tyr Phe
270                 275                 280                 285

Ser Thr Ala Leu Asp Ala Leu Asp Phe Phe His His Asp Tyr Gln Lys
                290                 295                 300

Ser Asn Ser Leu Ser Ser Asp Leu Asp Arg Arg Ile Ala Gln Asp Ser
            305                 310                 315

Val Ala Ala Ala Gly His Asp Tyr Leu Thr Ile Thr Ser Leu Ser Ile
        320                 325                 330
```

-continued

```
Arg Gln Ala Phe Ala Ala Thr Gln Leu Cys Gly Pro Ala Asn Asp Pro
335                 340                 345
Tyr Leu Phe Met Lys Glu Ile Ser Ser Asn Gly Asn Met Asn Thr Val
350                 355                 360                 365
Asp Val Ile Phe Pro Ala His Pro Val Phe Leu Tyr Thr Asn Pro Ala
                370                 375                 380
Leu Leu Lys Tyr Leu Leu Arg Pro His Leu Glu Ile Gln Glu Ser Gly
            385                 390                 395
Asn Tyr Pro Asn Ser Tyr Ala Met His Asp Ile Gly Ala His Tyr Pro
        400                 405                 410
Asn Ala Thr Gly His Pro Asp Gly Asn Asp Glu Pro Met Pro Leu Glu
    415                 420                 425
Glu Cys Gly Asn Met Val Ile Met Ala Leu Ala Tyr Ala Gln Lys Ala
430                 435                 440                 445
Gly Asp Thr Ala Tyr Leu Glu Ser His Tyr Thr Ile Leu Arg Arg Trp
                450                 455                 460
Thr Asp Tyr Leu Ile Glu Asp Ser Leu Tyr Pro Ala Asn Gln Ile Ser
            465                 470                 475
Thr Asp Asp Phe Ala Gly Pro Leu Ala Asn Gln Thr Asn Leu Ala Leu
        480                 485                 490
Lys Gly Ile Ile Gly Ile Glu Ala Met Ser Val Ile Ala Ser Leu Thr
    495                 500                 505
Gly Asp Ser Asp Asp Lys Met Asn Leu Thr Asn Tyr Ala His Asp Tyr
510                 515                 520                 525
Ile Glu Lys Trp Leu Ile Leu Gly Ile Ala Arg Asn Thr Thr Tyr Pro
                530                 535                 540
His Thr Thr Leu Ser Tyr Gly Ser Asn Glu Ser His Gly Leu Leu Tyr
            545                 550                 555
Asn Leu Tyr Ala Asp Arg Glu Leu Gly Leu Asn Leu Val Pro Gln Ser
        560                 565                 570
Val Tyr Asp Met Gln Ser Asn Phe Tyr Pro Thr Ile Lys Gly Gln Tyr
    575                 580                 585
Gly Val Pro Leu Asp Thr Arg His Gln Tyr Thr Lys Gly Asp Trp Glu
590                 595                 600                 605
Leu Phe Thr Ala Ala Val Ala Ser Val Ser Thr Arg Asp Met Phe Ile
                610                 615                 620
Lys Leu Leu Ala Gln Trp Ile Asn Glu Thr Pro Thr Asn Arg Pro Leu
            625                 630                 635
Thr Asp Leu Tyr Asp Thr Val Thr Gly Asp Tyr Pro Pro Val Val Phe
        640                 645                 650
Ile Ala Arg Pro Val Met Gly Ala Ala Phe Thr Leu Leu Leu Leu Asp
    655                 660                 665
```

<210> SEQ ID NO 23
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 23
gcttcataat tctcctgttg ttgagtc                                       27

<210> SEQ ID NO 24
<211> LENGTH: 30
<212> TYPE: DNA

-continued

```
<213> ORGANISM: ARTIFICIAL SEQUENCE
<220> FEATURE:
<223> OTHER INFORMATION: SYNTHETIC DNA

<400> SEQUENCE: 24
ggctataact gatgctatat actaccacac                                          30

<210> SEQ ID NO 25
<211> LENGTH: 2298
<212> TYPE: DNA
<213> ORGANISM: Aspergillus nidulans
<220> FEATURE:
<221> NAME/KEY: CDS
<222> LOCATION: (88)..(2151)
<223> OTHER INFORMATION:
<220> FEATURE:
<221> NAME/KEY: mat_peptide
<222> LOCATION: (145)..()
<223> OTHER INFORMATION:

<400> SEQUENCE: 25
gcttcataat tctcctgttg ttgagtcttt taaacggggc ctattagaag ggggttgcac         60
ggctgaggat cacctaccca gatcaat atg cgt act ttt cta cta ggc atc ctg       114
                               Met Arg Thr Phe Leu Leu Gly Ile Leu
                                                              -15 tgc gca ccc ctg gct atc ctt aca gga gcc gca tcg act ttt tct cca         162
Cys Ala Pro Leu Ala Ile Leu Thr Gly Ala Ala Ser Thr Phe Ser Pro
-10                  -5                  -1  1                 5 gca cgc cct ccg gct ctt cct cta gcg gtc aaa tct ccg tac ttg agt         210
Ala Arg Pro Pro Ala Leu Pro Leu Ala Val Lys Ser Pro Tyr Leu Ser
             10                  15                  20 act tgg ctg ccg gcg ggg aaa gac ggc ggc aat gga ggc tac ctt gca         258
Thr Trp Leu Pro Ala Gly Lys Asp Gly Gly Asn Gly Gly Tyr Leu Ala
         25                  30                  35 ggg gaa tgg cca gcg ttc tgg gaa ggc caa ata aca gga tgg gct ggc         306
Gly Glu Trp Pro Ala Phe Trp Glu Gly Gln Ile Thr Gly Trp Ala Gly
 40                  45                  50 ctt att cgt gtg gat ggc cag gtc tat aca tgg atg ggc ctt cca ggc         354
Leu Ile Arg Val Asp Gly Gln Val Tyr Thr Trp Met Gly Leu Pro Gly
55                  60                  65                  70 tca gcc act gtg aac cag act gcg tat gag tac act tca acg aag agc         402
Ser Ala Thr Val Asn Gln Thr Ala Tyr Glu Tyr Thr Ser Thr Lys Ser
                 75                  80                  85 att ttc acc atg cat att ggt gat atg gta gag atg aag ata acc ttc         450
Ile Phe Thr Met His Ile Gly Asp Met Val Glu Met Lys Ile Thr Phe
             90                  95                 100 ctt tca cca att aca ccg aat gat ctt cga cgg cag tcc cta gtg ttt         498
Leu Ser Pro Ile Thr Pro Asn Asp Leu Arg Arg Gln Ser Leu Val Phe
        105                 110                 115 tcg tat ctt gac gtg agt gtc acc tca ctc gac ggc cag tcc cac agt         546
Ser Tyr Leu Asp Val Ser Val Thr Ser Leu Asp Gly Gln Ser His Ser
    120                 125                 130 gta cag gtg tac gct gac ata tca gct gaa ttt gcg tct ggc gac cgt         594
Val Gln Val Tyr Ala Asp Ile Ser Ala Glu Phe Ala Ser Gly Asp Arg
135                 140                 145                 150 tcc gcc ata gca caa tgg aac tat ggt gtt acc agt gac ggc gta gcc         642
Ser Ala Ile Ala Gln Trp Asn Tyr Gly Val Thr Ser Asp Gly Val Ala
                155                 160                 165 tat cat aag atc tat cgc cag acg ccg ctc cta ttc tct gag cat aga         690
Tyr His Lys Ile Tyr Arg Gln Thr Pro Leu Leu Phe Ser Glu His Arg
            170                 175                 180 gac caa gct gaa tgg ggt gat tgg tac tgg gca act gac aat gta gca         738
Asp Gln Ala Glu Trp Gly Asp Trp Tyr Trp Ala Thr Asp Asn Val Ala
```

| | |
|---|---|
| Asp Gln Ala Glu Trp Gly Asp Trp Tyr Trp Ala Thr Asp Asn Val Ala<br>185                     190                      195 | |
| gga ctc act tac cag gct ggt cca gat gtt gat gtc cgg gaa gct ttt<br>Gly Leu Thr Tyr Gln Ala Gly Pro Asp Val Asp Val Arg Glu Ala Phe<br>    200                  205                     210 | 786 |
| gcg cgc aat gga aag cta acc aat aac aac gac gtc aac tac aga gct<br>Ala Arg Asn Gly Lys Leu Thr Asn Asn Asn Asp Val Asn Tyr Arg Ala<br>215                     220                     225                   230 | 834 |
| atc tcc aac aac tgg ccg gtg ttt ggt ttt gcc cat gac ctt ggg tct<br>Ile Ser Asn Asn Trp Pro Val Phe Gly Phe Ala His Asp Leu Gly Ser<br>                    235                     240                     245 | 882 |
| atc agc tct tct act aag gtg ctt ttc tca ata ggg cta acc cag cga<br>Ile Ser Ser Ser Thr Lys Val Leu Phe Ser Ile Gly Leu Thr Gln Arg<br>        250                     255                     260 | 930 |
| gag gca atc cag tat agc ggg aac tct tcc acc ctt tct cct ttg cct<br>Glu Ala Ile Gln Tyr Ser Gly Asn Ser Ser Thr Leu Ser Pro Leu Pro<br>            265                     270                     275 | 978 |
| gct ctg tgg acg agc tat ttc agc act gcc ttg gat gcc ctt gac ttc<br>Ala Leu Trp Thr Ser Tyr Phe Ser Thr Ala Leu Asp Ala Leu Asp Phe<br>280                     285                     290 | 1026 |
| ttc cac cat gat tat cag aag tca aac tct ctt tct tca gat ctt gat<br>Phe His His Asp Tyr Gln Lys Ser Asn Ser Leu Ser Ser Asp Leu Asp<br>295                    300                     305                   310 | 1074 |
| cgg cga att gca caa gat tcc gtt gcc gct gcc ggt cac gac tac ctt<br>Arg Arg Ile Ala Gln Asp Ser Val Ala Ala Ala Gly His Asp Tyr Leu<br>                  315                     320                     325 | 1122 |
| acc att aca tcc ctc agc att cgt caa gct ttc gct gca acc cag ctg<br>Thr Ile Thr Ser Leu Ser Ile Arg Gln Ala Phe Ala Ala Thr Gln Leu<br>            330                     335                     340 | 1170 |
| tgt ggg cca gca aat gat ccg tat ctc ttt atg aaa gaa atc tcc tcc<br>Cys Gly Pro Ala Asn Asp Pro Tyr Leu Phe Met Lys Glu Ile Ser Ser<br>                 345                     350                     355 | 1218 |
| aac ggc aac atg aac acg gta gat gtg atc ttc cct gct cat ccc gtc<br>Asn Gly Asn Met Asn Thr Val Asp Val Ile Phe Pro Ala His Pro Val<br>360                     365                     370 | 1266 |
| ttc tta tac aca aac cca gca ctg ctt aaa tat ctc ctg cgc cca cat<br>Phe Leu Tyr Thr Asn Pro Ala Leu Leu Lys Tyr Leu Leu Arg Pro His<br>375                    380                     385                   390 | 1314 |
| ttg gag atc cag gag tct gga aat tac ccc aac tcc tat gct atg cat<br>Leu Glu Ile Gln Glu Ser Gly Asn Tyr Pro Asn Ser Tyr Ala Met His<br>                  395                     400                     405 | 1362 |
| gat atc ggt gct cat tac cct aac gct aca ggc cat ccg gat ggc aat<br>Asp Ile Gly Ala His Tyr Pro Asn Ala Thr Gly His Pro Asp Gly Asn<br>                  410                     415                     420 | 1410 |
| gac gag cca atg ccg ttg gag gag tgc ggt aat atg gtg atc atg gct<br>Asp Glu Pro Met Pro Leu Glu Glu Cys Gly Asn Met Val Ile Met Ala<br>            425                     430                     435 | 1458 |
| cta gca tat gcg cag aag gcc ggg gac aca gcg tac ctg gaa agc cac<br>Leu Ala Tyr Ala Gln Lys Ala Gly Asp Thr Ala Tyr Leu Glu Ser His<br>440                     445                     450 | 1506 |
| tac aca ata ctg aga cgt tgg acg gac tac ttg atc gaa gat tct ctt<br>Tyr Thr Ile Leu Arg Arg Trp Thr Asp Tyr Leu Ile Glu Asp Ser Leu<br>455                    460                     465                   470 | 1554 |
| tat ccg gcg aac caa ata tcg aca gat gat ttc gca ggt cca ttg gca<br>Tyr Pro Ala Asn Gln Ile Ser Thr Asp Asp Phe Ala Gly Pro Leu Ala<br>                  475                     480                     485 | 1602 |
| aat caa acc aac ctc gcc ctg aag gga atc atc ggt atc gag gcc atg<br>Asn Gln Thr Asn Leu Ala Leu Lys Gly Ile Ile Gly Ile Glu Ala Met<br>            490                     495                     500 | 1650 |

-continued

```
tct gtc atc gct agc ctg aca gga gac tct gat gat aag atg aat ctc    1698
Ser Val Ile Ala Ser Leu Thr Gly Asp Ser Asp Asp Lys Met Asn Leu
        505                 510                 515 acc aat tac gcc cac gat tac atc gaa aaa tgg ctg att ttg gga att    1746
Thr Asn Tyr Ala His Asp Tyr Ile Glu Lys Trp Leu Ile Leu Gly Ile
    520                 525                 530 gca cgt aac aca acg tat ccg cat aca aca ttg tcg tac gga tca aac    1794
Ala Arg Asn Thr Thr Tyr Pro His Thr Thr Leu Ser Tyr Gly Ser Asn
535                 540                 545                 550 gag tct cat gga ctc ctg tac aac ctt tac gca gat cgc gag cta ggc    1842
Glu Ser His Gly Leu Leu Tyr Asn Leu Tyr Ala Asp Arg Glu Leu Gly
                555                 560                 565 ttg aac ctg gtc ccg caa tct gtg tat gac atg cag agc aac ttc tac    1890
Leu Asn Leu Val Pro Gln Ser Val Tyr Asp Met Gln Ser Asn Phe Tyr
            570                 575                 580 ccg aca atc aag ggt caa tac gga gtg cca ctg gat acc cgc cat caa    1938
Pro Thr Ile Lys Gly Gln Tyr Gly Val Pro Leu Asp Thr Arg His Gln
        585                 590                 595 tac acg aaa ggt gat tgg gag ctc ttc acg gcg gca gtc gca tca gta    1986
Tyr Thr Lys Gly Asp Trp Glu Leu Phe Thr Ala Ala Val Ala Ser Val
    600                 605                 610 agc aca cga gac atg ttc atc aaa cta ctt gcc cag tgg ata aac gag    2034
Ser Thr Arg Asp Met Phe Ile Lys Leu Leu Ala Gln Trp Ile Asn Glu
615                 620                 625                 630 acg cca acg aac cgt cca ctt acg gat ctc tat gac act gta acc gga    2082
Thr Pro Thr Asn Arg Pro Leu Thr Asp Leu Tyr Asp Thr Val Thr Gly
                635                 640                 645 gac tac cca ccg gta gtt ttc atc gct cga cct gtc atg ggc gcg gca    2130
Asp Tyr Pro Pro Val Val Phe Ile Ala Arg Pro Val Met Gly Ala Ala
            650                 655                 660 ttc act ttg ttg ctt ctc gac tgaaattctt tccaggtaca tacatgcttt       2181
Phe Thr Leu Leu Leu Leu Asp
        665 atcaggacaa aagagcggct aggcggtcca ttcccagtat ttgtgttaga tgtgatatat   2241 atggtcgtgt ttaagttgtg taatattgtg tggtagtata tagcatcagt tatagcc      2298

<210> SEQ ID NO 26
<211> LENGTH: 688
<212> TYPE: PRT
<213> ORGANISM: Aspergillus nidulans

<400> SEQUENCE: 26

Met Arg Thr Phe Leu Leu Gly Ile Leu Cys Ala Pro Leu Ala Ile Leu
                -15                 -10                  -5

Thr Gly Ala Ala Ser Thr Phe Ser Pro Ala Arg Pro Pro Ala Leu Pro
        -1   1               5                  10

Leu Ala Val Lys Ser Pro Tyr Leu Ser Thr Trp Leu Pro Ala Gly Lys
         15                 20                  25

Asp Gly Gly Asn Gly Tyr Leu Ala Gly Glu Trp Pro Ala Phe Trp
 30                  35                  40                 45

Glu Gly Gln Ile Thr Gly Trp Ala Gly Leu Ile Arg Val Asp Gly Gln
                 50                  55                  60

Val Tyr Thr Trp Met Gly Leu Pro Gly Ser Ala Thr Val Asn Gln Thr
             65                  70                  75

Ala Tyr Glu Tyr Thr Ser Thr Lys Ser Ile Phe Thr Met His Ile Gly
         80                  85                  90

Asp Met Val Glu Met Lys Ile Thr Phe Leu Ser Pro Ile Thr Pro Asn
     95                 100                 105
```

```
Asp Leu Arg Arg Gln Ser Leu Val Phe Ser Tyr Leu Asp Val Ser Val
110                 115                 120                 125

Thr Ser Leu Asp Gly Gln Ser His Ser Val Gln Val Tyr Ala Asp Ile
            130                 135                 140

Ser Ala Glu Phe Ala Ser Gly Asp Arg Ser Ala Ile Ala Gln Trp Asn
                145                 150                 155

Tyr Gly Val Thr Ser Asp Gly Val Ala Tyr His Lys Ile Tyr Arg Gln
            160                 165                 170

Thr Pro Leu Leu Phe Ser Glu His Arg Asp Gln Ala Glu Trp Gly Asp
        175                 180                 185

Trp Tyr Trp Ala Thr Asp Asn Val Ala Gly Leu Thr Tyr Gln Ala Gly
190                 195                 200                 205

Pro Asp Val Asp Val Arg Glu Ala Phe Ala Arg Asn Gly Lys Leu Thr
                210                 215                 220

Asn Asn Asn Asp Val Asn Tyr Arg Ala Ile Ser Asn Asn Trp Pro Val
            225                 230                 235

Phe Gly Phe Ala His Asp Leu Gly Ser Ile Ser Ser Thr Lys Val
        240                 245                 250

Leu Phe Ser Ile Gly Leu Thr Gln Arg Glu Ala Ile Gln Tyr Ser Gly
    255                 260                 265

Asn Ser Ser Thr Leu Ser Pro Leu Pro Ala Leu Trp Thr Ser Tyr Phe
270                 275                 280                 285

Ser Thr Ala Leu Asp Ala Leu Asp Phe Phe His His Asp Tyr Gln Lys
                290                 295                 300

Ser Asn Ser Leu Ser Ser Asp Leu Asp Arg Arg Ile Ala Gln Asp Ser
            305                 310                 315

Val Ala Ala Gly His Asp Tyr Leu Thr Ile Thr Ser Leu Ser Ile
        320                 325                 330

Arg Gln Ala Phe Ala Ala Thr Gln Leu Cys Gly Pro Ala Asn Asp Pro
    335                 340                 345

Tyr Leu Phe Met Lys Glu Ile Ser Ser Asn Gly Asn Met Asn Thr Val
350                 355                 360                 365

Asp Val Ile Phe Pro Ala His Pro Val Phe Leu Tyr Thr Asn Pro Ala
                370                 375                 380

Leu Leu Lys Tyr Leu Leu Arg Pro His Leu Glu Ile Gln Glu Ser Gly
            385                 390                 395

Asn Tyr Pro Asn Ser Tyr Ala Met His Asp Ile Gly Ala His Tyr Pro
        400                 405                 410

Asn Ala Thr Gly His Pro Asp Gly Asn Asp Glu Pro Met Pro Leu Glu
    415                 420                 425

Glu Cys Gly Asn Met Val Ile Met Ala Leu Ala Tyr Ala Gln Lys Ala
430                 435                 440                 445

Gly Asp Thr Ala Tyr Leu Glu Ser His Tyr Thr Ile Leu Arg Arg Trp
                450                 455                 460

Thr Asp Tyr Leu Ile Glu Asp Ser Leu Tyr Pro Ala Asn Gln Ile Ser
            465                 470                 475

Thr Asp Asp Phe Ala Gly Pro Leu Ala Asn Gln Thr Asn Leu Ala Leu
        480                 485                 490

Lys Gly Ile Ile Gly Ile Glu Ala Met Ser Val Ile Ala Ser Leu Thr
    495                 500                 505

Gly Asp Ser Asp Asp Lys Met Asn Leu Thr Asn Tyr Ala His Asp Tyr
510                 515                 520                 525
```

-continued

```
Ile Glu Lys Trp Leu Ile Leu Gly Ile Ala Arg Asn Thr Thr Tyr Pro
            530             535             540

His Thr Thr Leu Ser Tyr Gly Ser Asn Glu Ser His Gly Leu Leu Tyr
            545             550             555

Asn Leu Tyr Ala Asp Arg Glu Leu Gly Leu Asn Leu Val Pro Gln Ser
            560             565             570

Val Tyr Asp Met Gln Ser Asn Phe Tyr Pro Thr Ile Lys Gly Gln Tyr
    575             580             585

Gly Val Pro Leu Asp Thr Arg His Gln Tyr Thr Lys Gly Asp Trp Glu
590             595             600             605

Leu Phe Thr Ala Ala Val Ala Ser Val Ser Thr Arg Asp Met Phe Ile
            610             615             620

Lys Leu Leu Ala Gln Trp Ile Asn Glu Thr Pro Thr Asn Arg Pro Leu
            625             630             635

Thr Asp Leu Tyr Asp Thr Val Thr Gly Asp Tyr Pro Pro Val Val Phe
            640             645             650

Ile Ala Arg Pro Val Met Gly Ala Ala Phe Thr Leu Leu Leu Leu Asp
    655             660             665
```

GLUTAMINASE, ITS GENE AND A METHOD OF PRODUCING IT

This application is a divisional of U.S. application Ser. No. 10/262,083, filed on Oct. 2, 2002, now U.S. Pat. No. 6,830,905 which is a divisional of U.S. application Ser. No. 09/674,507, filed on Nov. 15, 2000, now abandoned which is a National Stage of PCT/JP99/02455, filed on May 12, 1999, which claims priority to: JP 10-134080, filed on May 15, 1998, JP 10-258974, filed on Sep. 11, 1998, JP 10-292443, filed on Oct. 14, 1998, and JP 11-89157, filed on Mar. 30, 1999.

TECHNICAL FIELD

The present invention relates a novel glutaminase and a gene encoding the same. The glutaminase of the present invention can be utilized as an enzyme for food processing to convert glutamine into glutamic acid exhibiting stronger "umami" taste (umami).

BACKGROUND ART

For the production of soy sauce, miso, and other natural seasonings containing protein hydrolysate products, koji mould (filamentous fungus belonging to the genus *Aspergillus*) has been utilized. For example, soy sauce is produced through two process steps of koji-making and fermentation. In the koji-making step, the starting material is principally degraded by enzymes produced by koji mould. In such a process, it is important to increase the amount of glutamic acid among various tasteful materials in order to obtain stronger umami of soy sauce.

Glutamic acid is produced through two kinds of pathways. The first is the liberation of glutamic acid from protein caused by protease and peptidase. The second is generation of glutamic acid through hydrolysis of glutamine catalyzed by glutaminase (glutamine amidohydrolase).

In the production of soy sauce, liberation ratio of glutamic acid relative to its content in the starting material is not so high, and this is considered to be due to insufficient glutaminase activity of koji mould. Therefore, breeding of strains exhibiting high activities of protease and glutaminase through cell fusion of high protease activity strain and high glutaminase activity strain in solid koji has also been attempted (Ushijima, S. et al., Agric. Biol. Chem., 51 (4), 1051 (1987), Japanese Patent Publication (KOKOKU) No. Hei 3-73271/1992).

As for glutaminase, those derived from various bacteria and animals have been well investigated (Wakayama, M. et al., J. Ferment. Bioeng., 82, No.6, 592–597 (1996), Chung-Bok, Mi, et al., Biochem. J., 324, 193–200 (1997), Duran, S. et al., Biochem. Genet., 34, 453–465 (1996)). On the other hand, investigation about glutaminase of koji mould had been retarded, but extracellular glutaminase and intracellular glutaminase have been purified from one strain of *Aspergillus oryzae*, and they have been characterized (Yano, T. et al., J. Ferment. Technol., Vol. 66, No. 2, 137–143 (1988)). These glutaminases have a molecular weight of about 113,000, and substantially similar properties.

Further, there have been determined an amino acid sequence of N-terminal region of glutaminase derived from *Aspergillus oryzae* HG strain (Fukuoka Industrial Technology Center, Institute of Biology and Food, Research Summary of 1996 (199)), and amino acid sequence within N-terminal region of glutaminase derived from *Aspergillus oryzae* (Food Research Institute, Aichi Prefectural Government, Japan, Annual Report of 1995 (Research Report) pp. 3–4, (1996)) for purified glutaminases.

Meanwhile, because koji mould is excellent in the ability for secreting extracellular proteins, it has been attracted attention as a host for the production of recombinant proteins, and practically used for some enzymes.

DISCLOSURE OF THE INVENTION

As described above, koji mould has already afforded results as a material for genetic recombination technology, and its glutaminase has also been investigated to some extent. However, it cannot be considered to be fully investigated, and its further investigation has been desired. In addition, any genes encoding glutaminase of koji mould have not been isolated.

The present invention has been accomplished in view of the aforementioned state of the art, and its object is to provide a gene encoding glutaminase derived from koji mould.

The present inventors successfully purified glutaminase from *Aspergillus oryzae*, determined its partial amino acid sequence, and isolated DNA coding for the glutaminase based on the obtained information, and thus the present invention has been completed. Further, they also succeeded in isolating DNA encoding glutaminase of *Aspergillus nidulans*.

That is, the present invention provides the followings:

(1) a protein defined in any of the following (A) to (D):

(A) a protein having an amino acid sequence represented by the amino acid numbers 1–670 of SEQ ID NO: 2 in Sequence Listing;

(B) a protein having an amino acid sequence represented by the amino acid numbers 1–669 of SEQ ID NO: 22 in Sequence Listing;

(C) a protein having an amino acid sequence represented by the amino acid numbers 1–670 of SEQ ID NO: 2 in Sequence Listing with substitution, deletion, insertion, addition or inversion of one or a plurality of amino acids, and having activity for catalyzing hydrolysis of glutamine to glutamic acid and ammonia;

(D) a protein having an amino acid sequence represented by the amino acid numbers 1–669 of SEQ ID NO: 22 in Sequence Listing with substitution, deletion, insertion, addition or inversion of one or a plurality of amino acids, and having activity for catalyzing hydrolysis of glutamine to glutamic acid and ammonia;

(2) a DNA which encodes a protein defined in any of the following (A) to (D):

(A) a protein having an amino acid sequence represented by the amino acid numbers 1–670 of SEQ ID NO: 2 in Sequence Listing;

(B) a protein having an amino acid sequence represented by the amino acid numbers 1–669 of SEQ ID NO: 22 in Sequence Listing;

(C) a protein having an amino acid sequence represented by the amino acid numbers 1–670 of SEQ ID NO: 2 in Sequence Listing with substitution, deletion, insertion, addition or inversion of one or a plurality of amino acids, and having activity for catalyzing hydrolysis of glutamine to glutamic acid and ammonia;

(D) a protein having an amino acid sequence represented by the amino acid numbers 1–669 of SEQ ID NO: 22 in Sequence Listing with substitution, deletion, insertion, addition or inversion of one or a plurality of amino acids, and having activity for catalyzing hydrolysis of glutamine to glutamic acid and ammonia;

(3) the DNA of (2) which is a DNA defined in any of the following (a) to (d)

(a) a DNA which contains nucleotide sequences represented by the nucleotide numbers 1174–1370, 1446–1741, 1800–2242, 2297–2880, 2932–3134, 3181–3324, 3380–3515, 3562–3628 of the nucleotide sequence of SEQ ID NO: 1 in Sequence Listing in this order;

(b) a DNA which contains nucleotide sequences represented by the nucleotide numbers 1807–2000, 2061–2353, 2412–2854, 2915–3498, 3554–3756, 3806–3949, 3996–4131, 4180–4246 of the nucleotide sequence of SEQ ID NO: 21 in Sequence Listing in this order;

(c) a DNA which hybridizes with the DNA of (a) under a stringent condition, and encodes a protein having activity for catalyzing hydrolysis of glutamine to glutamic acid and ammonia;

(d) a DNA which hybridizes with the DNA of (b) under a stringent condition, and encodes a protein having activity for catalyzing hydrolysis of glutamine to glutamic acid and ammonia;

(4) the DNA of (2) which has a nucleotide sequence shown in SEQ ID NO: 1 or SEQ ID NO: 17;

(5) the DNA of (3) which has a nucleotide sequence shown in SEQ ID NO: 21 or SEQ ID NO: 25;

(6) a recombinant vector comprising the DNA of (2) inserted in a vector;

(7) a transformant of microorganism introduced with the DNA of (2) in such a manner that the DNA can be expressed to produce glutaminase;

(8) the transformant of (7) which is derived from a filamentous fungus or bacterium belonging to the genus *Escherichia*; and (9) a method for producing glutaminase which comprises cultivating the transformant of (7) in a culture medium to produce glutaminase in the culture.

The term "glutaminase activity" used in this specification means activity for catalyzing hydrolysis of L-glutamine to L-glutamic acid and ammonia, and the activity may include activity for catalyzing hydrolysis of D-glutamine to D-glutamic acid and ammonia. The activity may also include activities for catalyzing hydrolysis of L-glutamine to L-glutamic acid and ammonia, and D-glutamine into D-glutamic acid and ammonia, and activity for catalyzing transfer reaction or hydrolysis reaction of glutamyl group of L-γ-glutamyl compounds. In the present specification two embodiments are disclosed as the glutaminase of the present invention. One or both of the embodiments, or equivalents thereof may occasionally be referred to as glutaminase of the present invention. Also, the DNA which encodes the glutaminase of the present invention may occasionally be referred to as glutaminase gene.

The glutaminase of the present invention is distinguished from known glutaminases derived from koji mould based on enzymological properties, and therefore it is considered a novel glutaminase.

The present invention will be explained in detail hereinafter.

<1> Glutaminase of the Present Invention

The glutaminase of the present invention can be obtained from culture of *Aspergillus oryzae* RIB40 (ATCC 42149) by purifying it, for example, as follows.

*Aspergillus oryzae* RIB40 (ATCC 42149) is cultured with wheat bran, and the obtained bran koji is immersed in a buffer solution to prepare a crude enzyme extract. This crude enzyme extract is subjected to freeze and thawing, and insoluble fractions are removed to obtain a supernatant. This supernatant is subjected to ammonium sulfate fractionation to obtain a fraction not precipitated with 55% saturated ammonium sulfate but precipitated with 85% saturated ammonium sulfate. The ammonium sulfate is removed from this fraction, and resultant can further be fractionated by anion exchange chromatography, hydrophobic chromatography, and gel filtration chromatography to provide purified glutaminase. As resins for the chromatographies, there are exemplified DEAE-TOYOPEARL (Tosoh) for the anion exchange chromatography, Phenyl Sepharose (Pharmacia) for the hydrophobic chromatography, and Superdex (Pharmacia) for the gel filtration chromatography. These purification procedures may be repeatedly performed.

In each step for purification of glutaminase, the desired fraction is selected based on the glutaminase activity. The glutaminase activity can be determined by a modified version of the method of Hartman (Hartman, S. C., J. Biol. Chem., 243, 853–863 (1968), the hydroxamate method).

Enzymological properties of the glutaminase obtained from bran koji of *Aspergillus oryzae* RIB40 (ATCC 42149) as described above are shown in Table 1 together with enzymological properties of known glutaminases, one derived from of *Aspergillus oryzae* (Yano, T. et al., J. Ferment. Technol., Vol. 66, No. 2, 137–143 (1988)), and one derived from *Bacillus subtilis* (Shimazu, H. et al., J. Brew. Soc. Japan, 86, No. 6, 441–446 (1991)).

TABLE 1

Enzymological properties of glutaminase of the present invention and known glutaminases

| | Glutaminase of The present invention | Derived from *A. Oryzae* Yano, T. et al. | Derived from *B. subtilis* Shimazu, H. et al. |
|---|---|---|---|
| Molecular weight | 82,090[1] | 113,000[2] | 55,000 |
| Optimum pH | pH 9 | pH 9 | PH 6 |
| PH stability | pH 7 | pH 9 | PH 5–8 |
| Optimum temperature | 37–45° C. | 45° C. | 50° C. |
| Temperature Stability | 0–45° C. | 0–37° C. | 0–45° C. |
| Salt Tolerance[3] | 50% at 5% NaCl 20% at 18% NaCl | 50% at 5% NaCl 10% at 18% NaCl | 100% at 10% NaCl 85% or more at 25% NaCl |
| Substrate Specificity[4] | L-Gln (100%) D-Gln (106%) L-Asn (97%) D-Asn (104%) | L-Gln (100%) D-Gln (2%) L-Asn (0%) D-Asn (0%) | L-Gln (100%) D-Gln (67%) L-Asn (0%) D-Asn (0%) |
| Reaction Specificity | γ-Glu-p-NA | γ-Glu-p-NA | γ-Glu-p-NA (not tested) |
| Transfer[5] | (10%) | (0%) | (0%) |
| Hydrolysis[6] | (16%) | (131%) | (0%) |
| Km value | $1.24 \times 10^{-3}$ M | $9.6 \times 10^{-5}$ M | $6.4 \times 10^{-4}$ M |

[1]Measured by MALDI-TOFMS
[2]Measured by gel filtration
[3]Relative values based on the activity in the absence of NaCl that is defined as 100%
[4]Relative values of activity for D-glutamic acid (D-Gln) based on the activity for L-glutamic acid (L-Gln) that is defined as 100%
[5]L-γ-glutamyl-p-nitroanilide + GlyGlu → L-γ-glutamyl-GlyGlu + p-nitroanilide
[6]L-γ-glutamyl-p-nitroanilide + $H_2O$ → L-glutamate + p-nitroanilide Based on the marked differences in enzymological properties shown above, in particular in the substrate specificity, the glutaminase of the present invention is concluded to be novel, and different from the known glutaminase derived from *Aspergillus oryzae*.

While the glutaminase of the present invention can be obtained by purifying it from culture of *Aspergillus oryzae* as described above, it can also be produced by expression of glutaminase gene of *Aspergillus oryzae* described below in a suitable host as will be described hereinafter.

As will be described hereinafter, the glutaminase derived from *Aspergillus oryzae* is expected to have the amino acid sequence represented by the amino acid numbers 1–670 in SEQ ID NO: 2 based on the nucleotide sequence of glutaminase gene. The molecular weight calculated from this amino acid sequence is about 76,000, and from its comparison with the value of molecular weight measured by MALDI-TOFMS, the glutaminase of the present invention is expected to be a glycoprotein.

The glutaminase of another embodiment of the present invention is derived from *Aspergillus nidulans*. The glutaminase derived from *Aspergillus nidulans* may be produced by purifying from a culture of *Aspergillus nidulans* in the same manner as described above, or expressing the glutaminase gene of *Aspergillus nidulans* in an appropriate host. The glutaminase derived from *Aspergillus nidulans* has deduced amino acid sequence represented by the amino acid numbers 1–669 of SEQ ID NO: 22 from the nucleotide sequence of the glutaminase gene.

As for the glutaminase of the present invention, so long as it has activity for catalyzing hydrolysis of glutamine to glutamic acid and ammonia, the aforementioned amino acid sequence may have substitution, deletion, insertion, addition or inversion of one or a plurality of amino acids.

The present invention also provides, as an embodiment of the glutaminase of the present invention, glutaminase of *Aspergillus nidulans* having the amino acid sequence shown in SEQ ID NO: 22. This glutaminase can be produced by purifying it from culture of *Aspergillus nidulans* in a manner similar to that described above, or by expression of glutaminase gene of *Aspergillus nidulans* in a suitable host.

<2> DNA of the Present Invention

The DNA of the present invention can be obtained from genomic DNA of *Aspergillus oryzae* RIB40 (ATCC 42149), for example, as follows.

A partial amino acid sequence of the purified glutaminase is determined, and oligonucleotide primers for PCR (polymerase chain reaction) are synthesized based on the obtained information of the amino acid sequence to perform PCR using genomic DNA prepared from fungal cells of *Aspergillus oryzae* RIB40 (ATCC42149) as template. Partial sequences determined in the working examples of the present invention to be described hereinafter are shown in SEQ ID NOS: 3–10. Among these sequences, SEQ ID NO: 3 is an N-terminal amino acid sequence of the glutaminase protein, and the other sequences are internal amino acid sequences of the glutaminase. The amino acid sequences shown in SEQ ID NOS: 5 and 8 were not present in the amino acid sequence of glutaminase expected from the glutaminase gene. The third Ala and the ninth Thr in the amino acid sequence shown in SEQ ID NO: 7 were replaced by Thr and Ser respectively in the amino acid sequence of glutaminase expected from the glutaminase gene, and it was considered that they were reading errors in peptide sequencer.

The genomic DNA can be obtained by the method of Gomi (Gomi, K. et al., J. Gen. Appl. Microbiol., 35, 225 (1989)).

By using oligonucleotides having nucleotide sequences shown in SEQ ID NO: 11 and SEQ ID NO: 12 of Sequence Listing as the primers, a DNA fragment of about 230 bp can be obtained by the aforementioned PCR.

Then, plaque hybridization is performed for a genomic DNA library of *Aspergillus oryzae* RIB40 (ATCC 42149) utilizing λ phage as a vector by using the DNA fragment amplified by PCR as a DNA probe to obtain positive clones.

Within the cloned fragment obtained as described above, nucleotide sequence of a portion having a length of about 4 kb within a region having about 4.8 kb (XhoI fragment) is determined, and the result is shown in SEQ ID NO: 1 of Sequence Listing. In SEQ ID NO: 1, the amino acid sequence encoded by nucleotides of the nucleotide numbers 1234–1284 corresponds to the amino acid sequence of the amino acid numbers 1–17 in the N-terminal amino acid sequence of the glutaminase protein shown in SEQ ID NO: 3. The amino acid sequences shown in SEQ ID NOS: 4, 6, 7, 9 and 10 respectively correspond to the amino acid sequences encoded by nucleotides of the nucleotide numbers 2618–2647, 2762–2803, 2804–2848, 2957–2986, and 2576–2605 of the nucleotide sequence shown in SEQ ID NO: 1.

From the above, it is clear that DNA having the nucleotide sequence shown in SEQ ID NO: 1 is a glutaminase gene.

From the comparison of the nucleotide sequence shown in SEQ ID NO: 1 and the nucleotide sequence of glutaminase cDNA to be described hereinafter, it was found that the nucleotide sequence of SEQ ID NO: 1 contained 8 exons (nucleotide numbers 117.4 or 1135–1370, 1446–1741, 1800–2242, 2297–288.0, 2932–3134, 3181–3324, 3380–3515, and 3562–3628), and these exons encoded an amino acid sequence comprised of 690 residues. This amino acid sequence is shown in SEQ ID NOS: 1 and 2. From the comparison of this amino acid sequence and the amino acid sequence of the N-terminal of the glutaminase protein shown in SEQ ID NO: 3, it is estimated that the sequence of the amino acid numbers −20 to −1 is a signal peptide, and the sequence of the amino acid numbers 1–670 is the mature protein in SEQ ID NO: 2. While the initiation codon is estimated to be ATG of the nucleotide numbers 1174–1176, the possibility that it consists of ATG at the nucleotide numbers 1135–1138 cannot be denied.

From the above, it is strongly suggested that DNA having the nucleotide sequence shown in SEQ ID NO: 1 contains a promoter and a region encoding glutaminase (including signal peptide).

The DNA of the present invention may be DNA of the nucleotide sequence shown in SEQ ID NO: 1 of which introns are removed, i.e., DNA comprising nucleotide sequences of nucleotide numbers 1174–1370, 1446–1741, 1800–2242, 2297–2880, 2932–3134, 3181–3324, 3380–3515 and 3562–3628 in this order, so long as it encodes the glutaminase of the present invention. Such DNA can be obtained, for example, as cDNA of the aforementioned glutaminase gene.

Glutaminase cDNA can be obtained, for example, from a cDNA library prepared from poly(A) RNA of *Aspergillus oryzae* by hybridization which utilizes DNA having the nucleotide sequence of SEQ ID NO: 1 or a part thereof (e.g., the aforementioned probe of about 230 bp).

Glutaminase cDNA can also be obtained by PCR utilizing oligonucleotides having the nucleotide sequences of SEQ ID NOS: 13 and 14 as primers, and by 3'-RACE utilizing oligonucleotides having the nucleotide sequences of SEQ ID NOS: 15 and 16 as primers. An exemplary nucleotide sequence of cDNA obtained from a highly glutaminase productive strain of *Aspergillus oryzae* is shown in SEQ ID NO: 17 of Sequence Listing. The amino acid sequence deduced from this nucleotide sequence is shown in SEQ ID NOS: 17 and 18. When the nucleotide sequence of this cDNA was compared with the sequence of the coding region in the genomic gene obtained in Example 2, they were identical except that "C" at the nucleotide number 54 of the cDNA (SEQ ID NO: 17) was "G" (nucleotide number 1227) in the genomic gene (SEQ ID NO: 1). This difference between the nucleotide sequences of the cDNA and the genomic gene is estimated to be due to difference of gene sequence between the strains.

The DNA of the present invention may be any one encoding glutaminase, and it includes, in addition to DNA having the nucleotide sequence shown in SEQ ID NO: 1 or SEQ ID NO: 17, those DNA of which unnecessary portions in 5' region have been removed. Depending on purpose of the use, it may be one encoding only the mature protein. DNA of which one or more codons encoding amino acids in the coding region are replaced with equivalent codons encoding the same amino acids is included in the DNA of the present invention. Further, the DNA of the present invention may be one encoding glutaminase having substitution, deletion, insertion, addition or inversion of one or a plurality of amino acids at one or a plurality of sites, so long as the activity of glutaminase is not degraded. The number of the amino acid meant by the expression "a plurality of" may vary depending on the location or kinds of amino acid residues in the three-dimensional structure of the glutaminase protein, but it may be usually 2–300, preferably 2–170, more preferably 2–50, most preferably 2–10.

As will be described hereinafter, the amino acid sequence of glutaminase of *Aspergillus oryzae* shown in SEQ ID NO: 2 and the amino acid sequence of glutaminase of *Aspergillus nidulans* shown in SEQ ID NO: 22 have about 73% of homology, and about 170 amino acid residues are different between them as for the mature protein portion.

DNA encoding a protein substantially the same as glutaminase such as those mentioned above can be obtained by modifying the nucleotide sequence of glutaminase gene, for example, by the site-specific mutagenesis so that amino acids should be substituted, deleted, inserted or added at a particular site. Such modified DNA as mentioned above may also be obtained by a conventionally known mutagenesis treatment. As such a mutagenesis treatment, there can be mentioned a method comprising treating DNA encoding glutaminase with hydroxylamine or the like in vitro, and a method comprising irradiating a bacterium belonging to the genus *Escherichia* with ultraviolet light, or treating it with a mutagenic agent conventionally utilized for mutagenesis such as N-methyl-N'-nitro-N-nitrosoguanidine (NTG), and nitrous acid.

The substitution, deletion, insertion, addition and inversion mentioned above include those due to difference among strains, and naturally occurring mutations.

DNA encoding a protein substantially the same as glutaminase can be selected by expressing DNA having mutations as described above in a suitable cell, and examining the expression product for glutaminase activity. DNA encoding a protein substantially the same as glutaminase can also be obtained by isolating DNA which hybridizes with DNA having any one of nucleotide sequences of nucleotide numbers 1174–1370, 1446–1741, 1800–2242, 2297–2880, 2932–3134, 3181–3324, 3380–3515, and 3562–3628 in the nucleotide sequence of SEQ ID NO: 1 in Sequence Listing, or DNA having the nucleotide sequence of the nucleotide numbers 1–2070 in the nucleotide sequence of SEQ ID NO: 17 under a stringent condition, and encodes a protein having the glutaminase activity. The term "stringent condition" herein used means a condition where so-called specific hybrids may be formed, but non-specific hybrids are not formed. While it is difficult to definitely define this condition numerically, examples of such condition include, for example, a condition where DNAs having high homology, e.g., homology of 65% or more may hybridize with each other, but DNAs having homology lower than that may not hybridize with each other, and a condition where hybridization is performed at a salt concentration corresponding to that of washing step of usual Southern hybridization, i.e., 1×SSC, 0.1% SDS, preferably 0.1×SSC, 0.1% SDS. Genes which hybridize under such a condition may also include those having a stop codon generated to interrupt the coding sequence, those having lost their activity due to mutation at the active center and the like, but they can easily be removed by ligating the genes to a commercially available active expression vector, and determining glutaminase activity by the method described hereinafter.

The DNA of the present invention can also be obtained from chromosome DNA or cDNA of microorganism of another species belonging to the genus *Aspergillus*, for example, *Aspergillus nidulans*. Specifically, it can be obtained from a chromosome DNA library of *Aspergillus nidulans*, for example, *Aspergillus nidulans* A26 strain by hybridization. A probe for the hybridization can be prepared by synthesizing oligonucleotide primers for PCR based on the aforementioned nucleotide sequence of the glutaminase gene of *Aspergillus oryzae*, and performing PCR using genome DNA prepared from cells of *Aspergillus nidulans*, e.g., *Aspergillus nidulans* A26 strain as template. As the primers for PCR, oligonucleotides having nucleotide sequences of SEQ ID NOS: 19 and 20 can be mentioned.

The nucleotide sequence and the amino acid sequence of the glutaminase gene of *Aspergillus nidulans* A26 obtained in the working examples to be described hereinafter in the manner described above are shown in SEQ ID NO: 21. The amino acid sequence is also shown in SEQ ID NO: 22. The homology between the glutaminase gene of *Aspergillus nidulans* and the glutaminase gene of *Aspergillus oryzae* was about 58% for the whole gene, about 68% for the coding region, and about 73% for the encoded amino acid sequence.

Glutaminase cDNA can also be obtained from a cDNA library prepared from poly(A) RNA of *Aspergillus nidulans* by, for example, PCR using oligonucleotides having nucleotide sequences SEQ ID NOS: 23 and 24. An exemplary nucleotide sequence of cDNA obtained from *Aspergillus nidulans* A26 is shown in SEQ ID NO: 25 of Sequence Listing. The amino acid sequence deduced from this nucleotide sequence is shown in SEQ ID NOS: 25 and 26.

The DNA of the present invention includes a DNA which encodes a protein having an amino acid sequence represented by the amino acid numbers 1–669 of SEQ ID NO: 22 in Sequence Listing with substitution, deletion, insertion, addition or inversion of one or a plurality of amino acids, and having activity for catalyzing hydrolysis of glutamine to glutamic acid and ammonia. The DNA of the present invention also includes a DNA which encodes a DNA which contains nucleotide sequences represented by the nucleotide numbers 1807–2000, 2061–2353, 2412–2854, 2915–3498, 3554–3756, 3806–3949, 3996–4131, 4180–4246 of the nucleotide sequence of SEQ ID NO: 21 in Sequence Listing in this order, and a DNA which hybridizes with the aforementioned DNA under a stringent condition, and encodes a protein having activity for catalyzing hydrolysis of glutamine to glutamic acid and ammonia.

The DNA of the present invention was obtained as described above in the wording examples to be described hereinafter. However, since its nucleotide sequence has been elucidated, it can easily be cloned by PCR, hybridization or the like from genomic DNA of *Aspergillus oryzae* RIB40

(ATCC 42149), *Aspergillus nidulans* A26, or other strains of *Aspergillus oryzae* and *Aspergillus nidulans*.

<3> Use of the DNA of the Present Invention

The DNA of the present invention can be utilized for breeding of filamentous fungi such as koji mould or production of glutaminase. For example, glutaminase activity can be enhanced by intracellularly introducing the DNA of the present invention, preferably as its multiple copies, into filamentous fungus. Glutaminase can be produced by expressing the DNA of the present invention in a suitable host. A filamentous fungus such as koji mould and glutaminase obtained as described above can be utilized for the production of soy sauce, miso, and other seasonings containing protein hydrolysate products.

As the filamentous fungus to be introduced with the DNA of the present invention, there can be mentioned filamentous fungi belonging to the genus *Aspergillus* such as *Aspergillus oryzae*, *Aspergillus niger* and *Aspergillus nidulans*, those belonging to the genus *Neurospora* such as *Neurospora crassa*, those belonging to the genus *Rhizomucor* such as *Rhizomucor miehei*, and the like.

The vector for introducing the DNA of the present invention into filamentous fungi such as those mentioned above is not particularly limited, and those usually used for the breeding of filamentous fungi and the like can be used. As those used for *Aspergillus oryzae*, there can be mentioned, for example, pUNG (Lee, B. R. et al., Appl. Microbiol. Biotechnol., 44, 425–431 (1995)), pMARG (Tsuchiya, K. et al., Appl. Microbiol. Biotechnol., 40, 327–332 (1993)), pUSC (Gomi, K. et al., Agric. Biol. Chem. 51, 2549–2555 (1987)) and the like. pUNG contains a marker complementing niaD⁻ (nitrate assimilation ability defficiency) of *Aspergillus oryzae* niaD300 (Minetoki, T. et al., Curr. Genet. 30, 432–438 (1996)), pMARG contains a marker complementing argB⁻ (arginine auxotroph) of *Aspergillus oryzae* M2-3 (Gomi, K. et al., Agric. Biol. Chem., 51(9), 2549–2555 (1987)), and pUSC contains a marker complementing sC⁻ (ATP sulfurylase defficiency) of *Aspergillus oryzae* NS4 (Yamada, O. et al., Biosci. Biotech. Biochem., 61(8), 1367–1369 (1997)).

Among these vectors, pUNG and pMARG contain a promoter of glucoamylase gene (glaA) and α-amylase gene (terminator of amyB), and the DNA of the present invention (region of the nucleotide numbers 1136–4777 or 1177–4777 in SEQ ID NO: 1) can be expressed in them under the control of the promoter to produce glutaminase by inserting the DNA into them in the downstream of the promoter in such a manner that the frames should be conformed. When pUSC is used, because pUSC does not contain a promoter, expression of the gene of the present invention can be obtained by introducing a plasmid such as pUC19 inserted with the DNA of the present invention and pUSC into a host filamentous fungus through co-transformation or them. Since the nucleotide sequences of SEQ ID NO: 1 is likely to contain a promoter as described hereinbefore, it is considered that glutaminase can be expressed even if the DNA of the present invention is inserted into the aforementioned vector together with a promoter.

Those vectors, promoters and markers described in the literature mentioned below can also be used depending on the host filamentous fungus. In Table 2, promoters are indicated by the enzyme names encoded by corresponding genes.

TABLE 2

| Literature | Promoter | Marker | Host filamentous fungus |
|---|---|---|---|
| International Patent Application Publication in Japanese (KOHYO) No. Hei 4-503450/1992 | Neutral α-amylase | | *Aspergillus niger* |
| | | argB | *Aspergillus niger* |
| | | argB | *Aspergillus nidulans* |
| | | trpC | *Aspergillus nidulans* |
| | | amdS | *Aspergillus nidulans* |
| | | pyr4 | *Neurospora crassa* |
| | | DHFR | *Neurospara crassa* |
| Japanese Patent Unexamined Publication (KOKAI) No. Sho 62-272988/1987 | Taka-amylase | | *Aspergillus oryzae* |
| | Aspartic protease | | *Rhizomucor miehei* |
| | Lipase | | *Rhizomucor miehei* |
| | Glucoamylase, lipase Amylase, glucoamylase, cellulase Protease, glycolytic pathway enzymes | | *Aspergillus niger* |
| Japanese Patent Unexamined Publication No. Hei 7-51067/1995 | Taka-amylase | | Genus *Aspergillus* |
| Japanese Patent Unexamined Publication No. Hei 7-115976/1995 | Novel promoter sequence is mentioned. | | *Aspergillus oryzae* |
| Japanese Patent Unexamined Publication No. Hei 7-59571/1995 | Novel promoter sequence is mentioned. | | *Aspergillus niger* |
| Journal of Japan Society for Bioscience, Biotechnology and Agrochemistry, Vol. 71, No. 10 (1997) 1018–1023 | α-amylase (amyB) | | *Aspergillus oryzae* |
| | Glucoamylase (glaA) | | *Aspergillus oryzae* |
| | Glucosidase (agdA) | | *Aspergillus oryzae* |

Transformation of filamentous fungi can be performed by the methods mentioned in the aforementioned literature as well as other known methods. Specifically, *Aspergillus oryzae*, for example, can be transformed as follows.

Fungal cells (conidiospores) are inoculated in DPY culture medium (2% glucose, 1% peptone, 0.5% yeast extract, pH 5.0), and cultured at 30° C. for around 24 hours with vigorous shaking. The culture medium is filtered through Myracloth (CALBIO CHEM), sterilized gauze or the like to collect the fungal cells, the cells are washed with sterilized water, and moisture is sufficiently removed from the cells. The cells are transferred into a test tube, added with an enzyme solution (1.0% Yatalase (Takara Shuzo), or 0.5% Novozyme (Novo Nordisk) and 0.5% cellulase (e.g., Cellulase Onozuka, Yakult), 0.6 M $(NH_4)_2SO_4$, 50 mM malic acid, pH 5.5), and gently shaken at 30° C. for around 3 hours. The degree of protoplastization is observed with a microscope, and they are stored on ice if they show good protoplastization.

The aforementioned enzymatic reaction mixture is filtered through Myracloth to remove the fungal cell residue, and the filtrate containing protoplasts is added with an equal volume of Buffer A (1.2 M sorbitol, 50 mM $CaCl_2$, 35 mM NaCl, 10 mM Tris-HCl, pH 7.5), and placed on ice. The mixture is centrifuged at 0° C. and 2,500 rpm for 8 minutes, and gently stopped, and the pellet is washed with Buffer A, and suspended in an optimum volume of Buffer A.

A DNA solution of not more than 20 µl (5–10 µg) is added to 100–200 µl of the protoplast suspension, and placed on ice for 20–30 minutes. To the mixture, 250 µl of Buffer B (polyethylene glycol 6000, 50 mM $CaCl_2$, 10 mM Tris-HCl, pH 7.5) is added and gently mixed, again 250 µl of Buffer B is added and gently mixed, further 850 µl of Buffer B is added and gently mixed, and then the mixture is left stand at room temperature for 20 minutes. Then, 10 ml of Buffer A is added to the mixture, and the test tube is inverted and subjected to centrifugation at 0° C. and 2,000 rpm for 8 minutes. Subsequently, the pellet is suspended in 500 µl of Buffer A.

A suitable amount of the above suspension is added to 5 ml top agar, which has been divided into fractions and warmed beforehand, overlaid on an under layer culture medium (selection medium containing 1.2 M sorbitol, which is prepared depending on the kind of marker), and cultured at 30° C. Grown fungal cells are transferred on the selection medium, and confirmed to be transformants. Recombinant DNA is prepared from the fungal cells. It is preferable to confirm that the DNA of the present invention is introduced into the recombinant DNA by restriction enzyme analysis, Southern analysis or the like.

When the transformants obtained as described above are cultured under a condition suitable for the promoter used, the glutaminase gene is expressed, and thus glutaminase is produced.

By allowing a culture of transformants that are introduced with the gene of the present invention and have enhanced glutaminase activity to react with protein, protein hydrolysis products having higher sodium glutamate content and stronger umami can be afforded. Examples of the protein to be reacted with the culture include, for example, those of soybean, wheat, wheat gluten and the like, and it may be those of defatted soybean, or any one of various proteins subjected to food processing such as swelling and solubilization, or proteins isolated from these various kinds of materials.

As for the condition of the reaction of the culture of transformants with the protein, for example, a starting material having a concentration of 0.2–50% may be mixed with a culture of transformants in the presence of a proteolytic enzyme, and allowed to react at 5–60° C. for 4 hours to 10 days.

After the completion of the reaction, insoluble unreacted proteins, fungal cells and the like can be removed by using conventional separation methods such as centrifugal separation or filtration. If required, the reaction mixture may be concentrated by vacuum concentration, reverse osmosis or the like, and the concentrate can be made into powder or granules by a drying process such as lyophilization, drying under reduced pressure, and spray drying. Thus, protein hydrolysates having high sodium glutamate content, and exhibiting stronger umami can be obtained without externally adding sodium glutamate.

DESCRIPTION OF PREFERRED EMBODIMENTS

The present invention will be explained more specifically with reference to the following examples hereinafter.

EXAMPLE 1

Purification of Glutaminase from *Aspergillus oryzae*

*Aspergillus oryzae* RIB40 (ATCC 42149) strain was cultured with wheat bran, and glutaminase was purified from the culture. In the purification step, glutaminase activity was determined by a modified version of the method of Hartman (Hartman, S. C., J. Biol. Chem., 243, 853–863 (1968), the hydroxamate method). That is, to 125µ of a solution containing 200 mM Tris-HCl (pH 7.0), 100 mM hydroxylamine hydrochloride, 50 mM L-glutamine, and 10 mM reduced glutathione, 25 µl of enzyme solution was added, and kept at 37° C. for 1 hour. Then, the mixture was added with 125 µl of a solution composed of a mixture of equal volumes of 3 N hydrochloric acid, 12% trichloroacetic acid solution and 5% $FeCl_3.6H_2O$ solution (dissolved in 0.1 N HCl), and absorption of the mixture at 525 nm was measured. As for the activity, the enzymatic activity which forms 1 µmol of L-glutamic acid γ-monohydroxamate at 37° C. per minute was defined as 1 unit.

(1) Cultivation

Wheat bran (Nisshin Flour Milling, 600 g), potassium phosphate (12 g), and distilled water (600 ml) were mixed well, introduced into six sets of deep Petri dish having a diameter of 15 cm in an amount of 160 g each, and autoclaved at 120° C. for 20 minutes to prepare culture medium.

To a slant culture of *Aspergillus oryzae* RIB40 (ATCC 42149) sufficiently forming spores, sterilized water (5 ml) was poured, and stirred to prepare a spore suspension. The suspension was inoculated to the above culture medium. The culture medium inoculated with the spores was mixed well, and cultured at 30° C. for 14 days. The culture medium was cared by stirring at 24 hours from the beginning of the cultivation.

(2) Extraction of Enzyme

The bran koji prepared as described above was immersed in three-fold volume of 20 mM potassium phosphate buffer (pH 7.4), 1 mM PMSF (phenylmethanesulfonyl fluoride), 0.1 mM EPNP (1,2-epoxy-3-(p-nitrophenoxy)propane), 1 mM EDTA, left stand at 4° C. for 16 hours, and subjected to filtration through gauze and centrifugal separation (4° C., 7,500 rpm for 30 minutes) to afford a supernatant, which was used as a crude enzyme extract.

(3) Fractionation by Ammonium Sulfate Precipitation

The crude enzyme extract was frozen at −80° C., and gradually thawed at 4° C., and insoluble fractions were removed by filtration. The resultant was added with ammonium sulfate (1010 g/2,880 ml) to afford a 55% saturated ammonium sulfate solution. The solution was stirred at 4° C. for 4 hours, and centrifuged (4° C., 7,500 rpm, 30 minutes) to remove the precipitates. The supernatant was further added with ammonium sulfate (703 g/3,180 ml) to afford an 85% saturated ammonium sulfate solution. The solution was stirred at 4° C. for 16 hours, and the produced precipitates were collected by centrifugation (4° C., 7,500 rpm, 30 minutes), and dissolved in 100 ml of 20 mM sodium phosphate buffer (pH 7.4). This was filtered through a filter having a pore diameter of 0.45 µm.

(4) Desalination 5 ml from 100 ml of the filtrate obtained in the above (3) was loaded on a column for desalination which had been preliminarily equilibrated with 20 mM potassium phosphate buffer (pH 7.4), 100 mM NaCl beforehand (HiTrap Desalting, Pharmacia, 5 ml×5), and eluted with the same buffer solution. This desalination procedure was performed 20 times each for 5 ml divided from 100 ml of the filtrate. The active fractions were combined to amount 300 ml, and concentrated and desalted to 50 ml by ultrafiltration.

(5) Anion Exchange Chromatography

The sample obtained above was adsorbed on a column filled with 250 ml DEAE-TOYOPEARL 650M (Tosoh), which had been preliminarily equilibrated with 20 mM potassium phosphate buffer (pH 7.4), and washed with the same buffer solution in a 4-fold volume of the column volume. After the washing, the column was eluted with linear gradient of NaCl increasing from 0 M to 0.5 M in the buffer of 8-fold volume of the column volume. The active fractions collected in the eluent (340 ml) was concentrated and desalted to 12 ml by ultrafiltration.

(6) Hydrophobic Chromatography

Then, fractionation by absorption chromatography was performed on a FPLC system (Pharmacia) utilizing HiLoad 26/10 Phenyl Sepharose High Performance (Pharmacia). This chromatographic procedure was performed twice for divided portions of the protein of DEAE-TOYOPEARL active fraction. 6 ml of the DEAE-TOYOPEARL active fraction added with 1 M ammonium sulfate was adsorbed on the column preliminarily equilibrated with 50 mM sodium phosphate buffer (pH 7.4), and 1 M ammonium sulfate, and the column was washed with the same buffer solution of 4-fold volume of the column volume. After the washing, the column was eluted with the buffer solution having linear ammonium sulfate gradient decreasing from 1 M to 0 M in 16-fold volume of the column volume. 300 ml of active fraction from the eluent was concentrated and desalted to 10 ml by ultrafiltration and centrifugal concentration (Centriprep 10, AMICON).

(7) Gel Filtration Chromatography

The above sample was subjected to fractionation by gel filtration chromatography on a FPLC system utilizing HiLoad 26/60 Superdex 200 pg (Pharmacia). This chromatographic procedure was performed 5 times for divided portions from the protein of the DEAE-TOYOPEARL active fraction. 2 ml of the active fraction obtained above was loaded on the column preliminarily equilibrated with 40 mM sodium phosphate buffer (pH 7.4), and 150 mM NaCl, and the column was eluted with the same buffer to collect active fraction. This gel filtration chromatography was repeated twice.

(8) Results of Purification

By the above-mentioned purification process, 500 μg of purified glutaminase was obtained. The molecular weight of the purified enzyme was determined by MALDI-TOFMS (Matrix assisted laser desorption ionization-time of flight mass spectrometer), and it was found to be 8,290. Total protein, total activity, specific activity, yield, and purity (based on the purity of the crude enzyme extract that was defined as 1) in various purification steps are summarized in Table 3.

TABLE 3

| Purification step | Glutaminase activity (Unit) | Amount of protein (mg) | Specific activity (unit/mg) | Yield (%) | Purity (fold) |
|---|---|---|---|---|---|
| Crude extract | 44.8 | 2528 | 0.018 | 100 | 1 |
| Freeze-thawing | 51 | 2230 | 0.023 | 114 | 1.28 |
| Ammonium sulfate precipitation | 16.2 | 665 | 0.024 | 36 | 1.33 |
| DEAE-TOYOPEARL | 7.2 | 186 | 0.039 | 16 | 2.2 |
| Phenyl Sepharose | 4.3 | 78.7 | 0.055 | 9.6 | 3.1 |
| First gel filtration | 0.8 | 1.1 | 0.73 | 1.6 | 39.4 |
| Second gel filtration | 0.4 | 0.5 | 0.88 | 1 | 48.9 |

(9) Determination of Partial Amino Acid Sequence of Glutaminase

The purified glutaminase (97 μg) in 500 mM Tris hydrochloric acid (pH 8.1), 6 M guanidine, and 2 mM EDTA was added with DTT (263 μg), substituted with nitrogen, and kept at 50° C. for 3 hours. The reduction reaction was performed at room temperature overnight while the reaction mixture was shielded from light. The mixture was further added with iodoacetic acid (2900 μg), allowed to react at room temperature for 30 minutes, and desalted on a Sephadex G-25 (Pharmacia) column. The desalted sample was concentrated on centrifugal concentration machine VC-960 (TAITEC), and added with 50 mM ammonium hydrogencarbonate (pH 8.5) and 1 μg lysyl endopeptidase (SIGMA) to perform limited degradation at 37° C. for 13 hours. After the reaction, the produced peptides were isolated by reversed-phase HPLC (Vydac Capillary $C_{18}$, Vydac), and each subjected to sequencing on a peptide sequencer PPSQ-10 (Shimazu Corporation) to determine internal partial amino acid sequences of glutaminase. Separately, the peptide not undergone the lysyl endopeptidase treatment was also subjected to sequencing on the peptide sequencer to determine its N-terminal amino acid sequence. The determined amino acid sequences are listed below.

```
N-terminal: ASTFSPARPPALPLAVK        (SEQ ID NO: 3)

No. 52:    Y(G/P)(N/V)(T/P)YAM(R/    (SEQ ID NO: 4)
           S)DI

No. 55:    VQY(T/G)EYDXY             (SEQ ID NO: 5)

No. 59:    DNDYLSQHYPILNK            (SEQ ID NO: 6)

No. 67:    WTAYLVEDTIYPANQ           (SEQ ID NO: 7)

No. 62.5:  VLLQSAIEGH                (SEQ ID NO: 8)

No. 63:    GIIGIQAMAV                (SEQ ID NO: 9)

No. 62:    XILKFXYXXQ                (SEQ ID NO: 10)
```

In the aforementioned sequences, "X" represents an indefinite amino acid, and "/" means that the corresponding amino acid is one indicated before or after it.

EXAMPLE 2

Cloning of Glutaminase Gene of Aspergillus oryzae

The glutaminase gene was isolated from a genomic library of Aspergillus oryzae by plaque hybridization.

(1) Production of Probe by PCR

From cells of Aspergillus oryzae RIB40, genome DNA was prepared as follows according to the method of Gomi (Gomi, K. et al., J. Gen. Appl. Microbiol., 35, 225 (1989)).

Spores of Aspergillus oryzae RIB40 from two slant culture tubes were suspended in 0.85% NaCl, inoculated in 1 L of YPD culture medium (2% glucose, 1% peptone, 0.5% yeast extract, pH 5.0), and cultured at 30° C. for 24 hours. The fungal cells were collected by filtration through gauze, immediately frozen with liquid nitrogen, and disrupted in a homogenizer (18000 rpm, 15 minutes) while cooling with liquid nitrogen or in a mortar. The resultant was added with 100 ml of 50 mM EDTA, 0.5% SDS, pH 8.0, and proteinase K to a final concentration of 0.1 mg/ml, and incubated at 50° C. for 4 hours. This solution was subjected to phenol treatment, phenol/chloroform treatment, and chloroform treatment twice each. These treatments with organic solvents were performed by gently mixing the solution and the organic solvents, and separating an aqueous layer.

The solution from which the protein had been removed as described above was added with 1/10 volume of 3 M sodium acetate (pH 5.2) and 2.5-fold volume or ethanol, left at −20° C. overnight, and centrifuged at 0° C. and 10,000 rpm for 20 minutes. The resulting precipitates were rinsed, and carefully dissolved in TE buffer. This solution was added with RNase A (10 μg/ml), and incubated at 37° C. for 30 minutes to degrade RNA. Then, the solution was mixed with ½ volume of phenol, left at 37° C. for 10 minutes, mixed with ½ volume of chloroform, and centrifuged at 0° C. and 10,000 rpm for 20 minutes to separate the aqueous layer. This aqueous layer was mixed with diethyl ether, and centrifuged at 0° C. and 10,000 rpm for 5 minutes, and the diethyl ether layer was removed to eliminate the phenol remained in the solution. The resulting aqueous layer was added with 3 M sodium acetate solution (500 μl) and ethanol (5 ml), left at −80° C. for one hour, and centrifuged at 10,000 rpm for 20 minutes to afford precipitates. These precipitates were rinsed, dissolved in TE buffer (5 ml), added with a small amount of chloroform, and stored under refrigeration.

After PCR using the genome DNA obtained as described above as template, and oligonucleotides which were synthesized based on the partial amino acid sequences (No. 52 and No. 67) and had the following sequences as primers, a partial sequence of glutaminase gene was obtained, and this was used as a probe for hybridization. The sequences of these primers were designed by referring to the codon frequency of Aspergillus nidulans (Andrew, T. Lloyd et al., Mol. Gen. Genet., 230, 288–294 (1991)).

The PCR reaction was performed by heat-denaturation at 95° C. for 9 minutes, and a cycle of 94° C. for 1 minute, 53° C. for 1 minute, and 72° C. for 1.5 minutes, which cycle was repeated for 35 cycles. This provided an about 230 b glutaminase gene fragment.

(2) Screening of Aspergillus oryzae Genomic Library

Screening of Aspergillus oryzae genomic library was performed by using the gene fragment obtained in the above PCR reaction as a probe.

The Aspergillus oryzae genome DNA was digested with BamHI into about 10 kb fragments, and they were inserted into BamHI site of λ phage vectors (λ DASH II, STRATAGENE). The obtained recombinant DNAs were in vitro packaged to construct a λ phage library.

Using the aforementioned λ phage library, about 5,000 plaques were formed per one plate having a diameter of 15 cm. Ten plates on which plaques were formed were prepared, and each plate was blotted to two pieces of nylon membranes (Hybond-N+, Amersham). That is, the nylon membranes were placed on the plate for 3 minutes for the first piece, or for 5 minutes for the second piece, and then placed on filter paper sheets soaked with a denaturation solution (1.5 M NaCl, 0.5 M NaOH) for 7 minutes. Then, the membranes were placed on filter paper sheets soaked with a neutralization solution (1.5 M NaCl, 0.5M Tris-HCl (pH 7.4)) for 3 minutes, and then on other filter paper sheets soaked with the same buffer for 3 minutes for neutralization, left stand in 2×SSC for 3 minutes, and air-dried. After the drying, the membranes were placed on filter paper sheets soaked with 0.4 M NaOH for 20 minutes, shaken in 5×SSC for 1 minute, and air-dried.

Each of the nylon membranes mentioned above was immersed into a pre-hybridization buffer (50% formamide, 5× Denhardt's solution, 5×SSPE, 0.5% SDS), and kept at 42° C. for 2 hours. The probe obtained in the PCR was labeled with [$^{32}$P-γ]-CTP using Random Label Kit (BOEHRINGER MANNHEIM). The labeled probe was kept at 100° C. for 3 minutes, immediately transferred on ice so that the DNA double strands should be denatured, and added to the pre-hybridization buffer, and the hybridization was performed at 42° C. overnight.

The aforementioned nylon membrane was subjected to washing in 2×SSC, 0.1% SDS at 65° C. for 15 minutes twice, washing in 1×SSC, 0.1% SDS at 65° C. for 15 minutes twice, and washing in 0.1×SSC, 0.1% SDS at 65° C. for 15 minutes twice. After the washing, the membrane was brought into contact with an imaging plate (FUJIX), and detected with an image analyzer BAS2000 (FUJIX). As a result, 21 positive signals were detected from about 50,000 plaques.

The 21 positive plaques were collected, and subjected to the second screening. In the second screening, about 50 plaques were formed on a plate having a diameter of 10 cm, and hybridization was performed in the same manner as in the first screening. Four kinds of positive plaques were detected in the second screening. The third screening was

```
(5' end primer)
TAC CCC AAC ACC TAT GCT ATG CGC GAT ATC          (SEQ ID NO: 11)

(3' end primer)
TTG GTT CGC CGG ATA AAT AGT ATC TTC GAC CAA GTA  (SEQ ID NO: 12)
``` performed in the same manner as in the second screening, and four kinds of positive clones were finally obtained.

Nucleotide sequencing of these four kinds of clones revealed that all of the clones contained the same sequence. The nucleotide sequence of XhoI fragment derived from one of the clones, and the amino acid sequence encoded by the nucleotide sequence are shown in SEQ ID NO: 1. The amino acid sequence alone is shown in SEQ ID NO: 2.

*Escherichia coli* DH5α strain which had been transformed with a plasmid obtained by inserting the aforementioned XhoI fragment into plasmid pBluescript was given a private number of AJ13495, and it was deposited at the National Institute of Bioscience and Human-Technology, Agency of Industrial Science and Technology, Ministry of International Trade and Industry (zip code: 305-8566, 1-3 Higashi 1-Chome, Tsukuba-shi, Ibaraki-ken, Japan) on Sep. 9, 1998, and received an accession No. FERM BP-6490.

EXAMPLE 3

Cloning of Glutaminase cDNA of *Aspergillus oryzae*

A highly glutaminase productive strain of *Aspergillus oryzae* was cultured in DPY culture medium (50 ml) at 30° C. for 48 hours. The fungal cells were collected by filtration through gauze to obtain 1 g of cells. The cells were immediately frozen with liquid nitrogen, and disrupted in a mortar, from which 0.2 mg of total RNA were obtained according to the guanidine-cesium chloride ultracentrifugation method (Molecular Cloning, 2nd edition, Cold Spring Harbor Press (1989)). From the total RNA, mRNA was purified by using mRNA Purification Kit (Pharmacia), and cDNA was synthesized with cDNA PCR Library Kit (Takara Shuzo). By using this kit, a CA cassette adapter sequence is ligated to the 5' end of the obtained cDNA, and an oligo dT-RA sequence to the 3' end.

By using the cDNA obtained as described above as template, and oligonucleotides synthesized based on the nucleotide sequence of glutaminase genome and having the following sequences as primers, the glutaminase cDNA was amplified by PCR and 3'-RACE.

EXAMPLE 4

Expression of Glutaminase cDNA in *Escherichia coli*

Lac promoter, T7 promoter or Trp promoter is ligated to the upstream of the glutaminase cDNA, and inserted into a multi-cloning site of pBluescript (Stratagene) *Escherichia coli* DH5α is transformed with the obtained recombinant plasmid in a conventional manner, and the obtained transformants are selected on an agar medium containing 50 μg/ml of ampicillin. The selected transformants are cultured at 37° C. in LB culture medium (1% trypton, 0.5% yeast extract, 1% NaCl) overnight. This culture medium (1 ml) is transferred into LB culture medium (50 ml), and cultured at 37° C. When its OD reaches 0.6 after 3 hours, IPTG (isopropyl-β-D-thiogalactopyranoside) is added to a final concentration of 1 mM to induce lac promoter, and the cultivation at 37° C. is further continued for 4 hours. After the cultivation, the cells are collected, suspended in a buffer, and sonicated to provide protein inclusion bodies. These inclusion bodies are dissolved in a denaturant solution (8 M urea, 10 mM DTT, 50 mM NaCl, 50 mM Tris-HCl (pH 8.0), 5 mM EDTA), and insoluble fractions are removed by centrifugation. Refolding of the protein can be achieved by gradually lowering the urea concentration in the solution of solubilized protein.

*Escherichia coli* DH5α strain which had been transformed with a plasmid obtained by inserting the aforementioned glutaminase cDNA fragment into plasmid pBluescript was given a private number of AJ13496, and it was deposited at the National Institute of Bioscience and Human-Technology, Agency of Industrial Science and Technology, Ministry of International Trade and Industry (zip code: 305-8566, 1-3 Higashi 1-Chome, Tsukuba-shi, Ibaraki-ken, Japan) on Sep. 9, 1998, and received an accession No. FERM BP-6491.

```
(5' end primer)
GAT CAT GAT GCA TTT CCT CTC GTT CTG TC   (SEQ ID NO: 13)

(3' end primer)
GCA AAG TCA TCC GTA GAG ATC TGG TTC G    (SEQ ID NO: 14)

(5' end primer for 3'-RACE)
GGC GAA CCA GAT CTC TAC GGA TGA CTT TGC  (SEQ ID NO: 15)

(3' end primer for 3'-RACE)
CTG ATC TAG ACC TGC AGG CTC            (SEQ ID NO: 16)
```

The PCR reactions were each performed by heat-denaturation at 95° C. for 9 minutes, and a cycle of 94° C. for 1 minute, 55° C. for 1 minute, and 72° C. for 1 minute, which cycle was repeated for 30 cycles. The PCR using the primers of SEQ ID NOS: 13 and 14 provided an about 1500 bp DNA fragment, and the 3'-RACE using the primers of SEQ ID NOS: 15 and 16 provided an about 780 bp DNA fragment.

The nucleotide sequence of these DNA fragments is shown in SEQ ID NO: 17. The amino acid sequence deduced from this nucleotide sequence is shown in SEQ ID NOS: 17 and 18.

EXAMPLE 5

Cloning of Glutaminase Gene of *Aspergillus nidulans*

(1) Production of Probe by PCR

Based on the nucleotide sequence of the glutaminase gene of *Aspergillus oryzae* determined in Examples 1 and 2, oligonucleotide primers for PCR were synthesized, and PCR was performed by using genome DNA prepared from cells of *Aspergillus nidulans* A26 as template. The genome DNA was prepared in the same manner as in Example 2 according to the method of Gomi (Gomi, K. et al., J. Gen. Appl. Microbiol., 35, 225(1989)).

Oligonucleotides having sequences of the nucleotide numbers 1952–1979 and 2839–2868 of SEQ ID NO: 1 in Sequence Listing were synthesized as the PCR primers.
(5' end primer) GAC GAC CAA GAT GGT CTG AGC TAC CAG T (1952–1979) (SEQ ID NO: 19)
(3' end primer) GCA AAG TCA TCC GTA GAG ATC TGG TTC GCC (2839–2868) (SEQ ID NO: 20)

The PCR reaction was performed by heat-denaturation at 95° C. for 3 minutes, and a cycle of 94° C. for 1 minute, 37° C. for 1 minute, and 72° C. for 1 minute, which cycle was repeated for 30 cycles. This provided an about 900 b glutaminase gene fragment.

(2) Screening of *Aspergillus nidulans* Genomic Library

Screening of *Aspergillus nidulans* genomic library was performed by using the gene fragment obtained in the above PCR reaction as a probe.

The *Aspergillus nidulans* genomic library was purchased from Fungal Genetics Strain Center (Kansas City, USA). Using this library, agar medium was prepared in a plate having a diameter of 10 cm, and a nylon membrane Hybond-N+ (Amersham) was overlaid thereon. The cells were inoculated on the nylon membrane to form about 50 colonies on one membrane. 30 pieces of plate on which the colonies were formed were prepared, and a nylon membrane was collected from each plate. Each nylon membrane was placed on a filter paper sheet soaked with a denaturation solution (1.5 M NaCl, 0.5 M NaOH) for 7 minutes. Then, the membrane was placed on a filter paper sheet soaked with a neutralization solution (1.5 M NaCl, 0.5M Tris-HCl (pH 7.4)) for 3 minutes, and then on another filter paper sheet soaked with the same buffer for 3 minutes for neutralization, left stand in 2×SSC for 3 minutes, and air-dried. After the drying, the membrane was placed on a filter paper sheet soaked with 0.4 M NaOH for 20 minutes, shaken in 5×SSC for 1 minute, and air-dried.

The nylon membrane mentioned above was soaked into a pre-hybridization buffer (50% formamide, 5× Denhardt's solution, 5×SSPE, 0.5% SDS), and kept at 65° C. for 2 hours. The probe obtained in the PCR was labeled with [$^{32}$P-γ]-CTP using Random Label Kit (BOEHRINGER MANNHEIM). The labeled probe was kept at 100° C. for 3 minutes, immediately transferred on ice so that the DNA double strands should be denatured, and added to the pre-hybridization buffer, and the hybridization was performed at 65° C. overnight.

The aforementioned nylon membrane was subjected to washing in 2×SSC, 0.1% SDS at 65° C. for 15 minutes twice, washing in 1×SSC, 0.1% SDS at 65° C. for 15 minutes twice, and washing in 0.1×SSC, 0.1% SDS at 65° C. for 15 minutes twice. After the washing, the membrane was brought into contact with an imaging plate (FUJIX), and detected with an image analyzer BAS2000 (FUJIX). As a result, 4 positive signals were detected from about 1500 colonies.

Nucleotide sequencing of these four kinds of clones revealed that all of the clones contained the same sequence. The nucleotide sequence of HindIII-EcoRV fragment derived from one of the clones, and the amino acid sequence encoded by the nucleotide sequence are shown in SEQ ID NO: 21. The amino acid sequence alone is shown in SEQ ID NO: 22.

*Escherichia coli* DH5α strain which had been transformed with a plasmid obtained by inserting the aforementioned HindIII-EcoRV fragment into plasmid pBluescript was given a private number of AJ13509, and it was deposited at the Fermentation Research Institute, Agency of Industrial Science and Technology, Ministry of International Trade and Industry (currently the National Institute of Bioscience and Human-Technology, Agency of Industrial Science and Technology, Ministry of International Trade and Industry) on Sep. 22, 1998, and received an accession No. FERM BP-6520.

EXAMPLE 6

Cloning of Glutaminase cDNA of *Aspergillus nidulans*

*Aspergillus nidulans* A26 was cultured in 50 ml of YG culture medium (0.5% yeast extract, 2.5% glucose, 0.1% trace elements*) at 37° C. for 21 hours with shaking. The cells were collected on a filter paper sheet, and cultured in a plate containing minimal medium (0.6% NaNO$_3$, 0.152% KH$_2$PO$_4$, 0.052% KCl, 0.052% MgSO$_4$.7H$_2$O, 1% glucose, 0.1% trace elements*, 2×10$^{-5}$% biotin, 1.5% agar) at 37° C. for 24 hours (trace elements*: 0.1% FeSO$_4$. 7H$_2$O, 0.88% ZnSO$_4$.7H$_2$O, 0.04% CuSO$_4$.5H$_2$O, 0.015% MnSO$_4$.4H$_2$O, 0.01% Na$_2$B$_4$O$_7$.10H$_2$O, 0.005% (NH$_4$)$_6$Mo$_7$O$_{24}$4H$_2$O).

The cells were collected from the plate, frozen with liquid nitrogen, and disrupted in a mortar. Total RNA was prepared using RNeasy Plant Mini Kit (QIAGEN) from the disrupted product, and mRNA was prepared from the total RNA using mRNA Purification Kit (Amersham Pharmacia Biotech). A cDNA library was prepared from the mRNA using cDNA Synthesis Kit and cDNA PCR Library Kit (Takara).

By using the cDNA library as template, and the following primers which had been designed based on the *Aspergillus nidulans* genomic DNA sequence, cloning of glutaminase cDNA was performed by PCR.

```
(5' end primer)
GCT TCA TAA TTC TCC TGT TGT TGA GTC      (SEQ ID NO: 23)
Anti-sense primer (3' end primer)
GGC TAT AAC TGA TGC TAT ATA CTA CCA CAC  (SEQ ID NO: 24)
```

The reactions of the PCR were performed by heat denaturation at 94° C. for 5 minutes, and 30 cycles of [94° C. for 30 seconds, 55° C. for 30 seconds, 72° C. for 2 minutes]. As a result, an amplified fragment of about 2300 bp was observed, and thus a full length glutaminase cDNA was successfully obtained. The nucleotide sequence of this DNA fragment is shown in SEQ ID NO: 25. The amino acid sequence deduced from this nucleotide sequence is shown in SEQ ID NO: 26.

*Escherichia coli* DH5α strain which had been transformed with a plasmid obtained by inserting the aforementioned *Aspergillus nidulans* glutaminase cDNA fragment into TA cloning site of pGEM T Easy Vector (Promega) was given a private number of AJ13575, and it was deposited at the National Institute of Bioscience and Human-Technology, Agency of Industrial Science and Technology, Ministry of International Trade and Industry (zip code: 305-8566, 1-3 Higashi 1-Chome, Tsukuba-shi, Ibaraki-ken, Japan) on Mar. 11, 1999, and received an accession No. FERM BP-6679.

EXAMPLE 7

Production of Glutaminase

The glutaminase gene containing a promoter sequence was ligated to a vector containing a marker gene sC to provide a vector for transformation. Transformation was performed by using 10 µg of this plasmid DNA.

Conidiospores were inoculated in DPY culture medium, and cultured at 30° C. for 24 hours with vigorous shaking. The culture medium was filtered through sterilized gauze, the cells were collected, and washed with sterilized water, and moisture was sufficiently removed from the cells. These cells were transferred to a test tube, added with an enzyme solution (20 ml, 1.0% Yatalase, Takara Shuzo), and gently shaken at 30° C. for 3 hours. The degree of protoplastization was observed with a microscope, and they are stored on ice.

The aforementioned enzymatic reaction mixture was filtered through Myracloth remove the cell residue, and the filtrate containing protoplasts was added with an equal volume of Buffer A (1.2 M sorbitol, 50 mM $CaCl_2$, 35 mM NaCl, 10 mM Tris-HCl, pH 7.5), and placed on ice. The mixture was centrifuged at 0° C. and 1,500 rpm for 5 minutes, and gently stopped, and the pellet was washed with Buffer A twice, and suspended in 1 ml of Buffer A.

A DNA solution (10 µl, 10 µg) was added to 100 µl of the protoplast suspension, and placed on ice for 30 minutes. To the mixture, 250 µl of Buffer B (60% PEG (polyethylene glycol) 6000, 50 mM $CaCl_2$, 10 mM Tris-HCl, pH 7.5) was added and gently mixed, then 250 µl of Buffer B was added again and gently mixed, and 850 µl of buffer B was further added and gently mixed, and the mixture was left stand at room temperature for 20 minutes. Then, 10 ml of Buffer A was added to the mixture, and the test tube was inverted and subjected to centrifugation at 0° C. and 1,500 rpm for 5 minutes. Then, the pellet was suspended in 500 µl of Buffer A.

The above suspension was added to 5 ml top agar culture medium, which had been divided into fractions and warmed beforehand, overlaid on M culture medium (1.2 M sorbitol, 0.2% ammonium chloride, 0.1% ammonium sulfate, 0.05% potassium chloride, 0.05% sodium chloride, 0.1% potassium dihydrogenphosphate, 0.05% magnesium sulfate heptahydrate, 0.002% ferrous sulfate, 2% glucose, pH 5.5), and cultured at 30° C. One strain of the grown cells was transferred on the M medium, and confirmed to be a transformant. Recombinant DNA was prepared from the cells, and it was confirmed that at least 2 copies of the DNA of the present invention existed by Southern analysis.

The transformant obtained above was cultured with wheat bran, and the glutaminase activity was measured for its extract. Wheat bran (Nisshin Flour Milling, 160 g), potassium phosphate (3.2 g), and distilled water (160 ml) were mixed well, introduced into a deep Petri dish having a diameter of 15 cm, and autoclaved at 120° C. for 20 minutes to prepare culture medium.

To a slant culture of the transformant sufficiently forming spores, sterilized water (10 ml) was poured, and stirred to prepare a spore suspension. The suspension was inoculated to the above culture medium. The culture medium inoculated with the spores was mixed well, and cultured at 30° C. for 14 days. The culture medium was cared by stirring at 24 hours from the beginning of the cultivation.

The bran koji prepared as described above was immersed in three-fold volume of 20 mM potassium phosphate buffer (pH 7.4), 1 mM PMSF (phenylmethanesulfonyl fluoride), 0.1 mM EPNP (1,2-epoxy-3-(p-nitrophenyxy)propane), 1 mM EDTA, left stand at 4° C. for 16 hours, and subjected to filtration through gauze and centrifugal separation (4° C., 15 minutes, 10,000 rpm) to provide a supernatant, which was used as a crude enzyme extract.

The glutaminase activity of this crude enzyme extract was determined. Another crude enzyme extract was similarly obtained from a transformant obtained by transforming a vector DNA having only the marker gene as control, and its glutaminase activity was measured.

TABLE 4

|  | Glutaminase activity (per koji mg) |
| --- | --- |
| Transformant | 1.43 U/mg |
| Control strain | 0.38 U/mg |

As a result, marked activity increase was observed in the strain that had been introduced with the gene of the present invention, and it was demonstrated that the introduced glutaminase was expressed and produced.

INDUSTRIAL APPLICABILITY

The present invention provides a novel gene encoding glutaminase derived from koji mould. This gene can be used for breeding of koji mould, production of glutaminase, and production of seasonings such as soy sauce.

What is claimed is:

1. An isolated protein with glutaminase activity encoded by a DNA, which hybridizes under stringent conditions to SEQ ID NO:21, wherein said stringent conditions comprise washing in 0.1×SSC and 0.1% SDS at 65° C. for 15 minutes.

2. A method of producing glutamic acid, comprising contacting glutamine with the isolated protein of claim 1, and thereby converting glutamine to glutamic acid.

3. An isolated protein with glutaminase activity encoded by a DNA, which hybridizes under stringent conditions to SEQ ID NO:25, wherein said stringent conditions comprise washing in 0.1×SSC and 0.1% SDS at 65° C. for 15 minutes.

4. A method of producing glutamic acid, comprising contacting glutamine with the isolated protein of claim 3, and thereby converting glutamine to glutamic acid.

5. An isolated protein comprising amino acids 1–669 of SEQ ID NO:22.

6. A method of producing glutamic acid, comprising contacting glutamine with the isolated protein of claim 5, and thereby converting glutamine to glutamic acid.

* * * * *